US007501494B2

(12) United States Patent
Lynn et al.

(10) Patent No.: US 7,501,494 B2
(45) Date of Patent: Mar. 10, 2009

(54) DESIGNED DEIMMUNIZED MONOCLONAL ANTIBODIES FOR PROTECTION AGAINST HIV EXPOSURE AND TREATMENT OF HIV INFECTION

(75) Inventors: Shugene Lynn, Taoyuan (TW); Chang Yi Wang, Cold Spring Harbor, NY (US)

(73) Assignee: United Biomedical, Inc., Hauppauge, NY (US)

( * ) Notice: Subject to any disclaimer, the term of this patent is extended or adjusted under 35 U.S.C. 154(b) by 614 days.

(21) Appl. No.: 10/342,959

(22) Filed: Jan. 15, 2003

(65) Prior Publication Data

US 2004/0137000 A1   Jul. 15, 2004

(51) Int. Cl.
*C07K 16/00* (2006.01)
*A61K 39/395* (2006.01)
(52) U.S. Cl. .................. 530/387.1; 424/130.1
(58) Field of Classification Search ............ 435/69.1, 435/70.21, 455, 326, 328, 334, 339, 339.1, 435/346; 530/388.1, 388.15, 388.22, 388.35
See application file for complete search history.

(56) References Cited

U.S. PATENT DOCUMENTS 5,912,176 A   6/1999   Wang ..................... 435/452

FOREIGN PATENT DOCUMENTS

| EP | 1 083 226 | 3/2001 |
| WO | WO 95/24483 | 9/1995 |
| WO | WO 98/52976 | 11/1998 |
| WO | WO 9852976 | 11/1998 |

OTHER PUBLICATIONS

Li et al. 2000, Biochemistry, vol. 39, p. 6296-6309.*
Moore, J.P. et al., Genetic subtypes, humoral immunity, and human immunodeficiency virus type 1 vaccine development. *J. Virol.* 2001, 75(13), 5721-5729.
Moore, J.P. AIDS vaccines: On the trail of two trials. *Nature* 2002, 415, 365-366.
Sawyer, L.S.W. et al., Neutralization sensitivity of human immunodeficiency virus type 1 is determined in part by the cell in which the virus is propagated. *J. Virol.* 1994, 68(3), 1342-1349.
Cheng-Mayer, C. et al., Biologic features of HIV-1 that correlate with virulence in the host. *Science* 1988, 240, 80-82.
Daar, E.S. et al., High concentrations of recombinant soluble CD4 are required to neutralize primary human immunodeficiency virus type 1 isolates. *Proc. Nat. Acad. Sci. USA* 1990, 87(17), 6574-6578.
Mascola, J.R., et al., Immunization with envelope subunit vaccine products elicits neutralizing antibodies against laboratory-adapted but not primary isolates of human immunodeficiency virus type 1. The National Institute of Allergy and Infectious Diseases AIDS Vaccine Evaluation Group. *J. Infect Dis* 1996, 173(2), 340-348.

Belshe, R.B. et al., Neutralizing antibodies to HIV-1 in seronegative volunteers immunized with recombinant gp120 from the MN strain of HIV-1. NIAID AIDS Vaccine Clinical Trials Network. *JAMA* 1994, 272(6), 475-480.
Keefer, M.C. et al., Studies of high doses of a human immunodeficiency virus type 1 recombinant glycoprotein 160 candidate vaccine in HIV type 1-seronegative humans. The AIDS Vaccine Clinical Trials Network. *AIDS Res Hum Retroviruses* 1994, 10(12), 1713-1723.
Hanson, C.V. Measuring vaccine-induced HIV neutralization: Report of a workshop. *AIDS Res Hum Retroviruses* 1994, 10(6), 645-648.
Desrosiers, R.C. et al., Vaccine protection against simian immunodeficiency virus infection. *Proc Nat Acad Sci USA* 1989, 86, 6353-6357.
Stott, E.J. Anti-cell antibody in macaques. *Nature* 1991, 353(6343), 393.
Gardner, M. et al., Passive immunization of rhesus macaques against SIV infection and disease. *AIDS Res Hum Retroviruses* 1995, 11(7), 843-854.
Sattentau, Q.J. et al., Epitopes of the CD4 antigen and HIV infection. *Science* 1986, 234, 1120-1123.
Jameson, B.D. et al., Location and chemical synthesis of a binding site for HIV-1 on the CD4 protein.*Science* 1988, 240, 1335-1339.
Reimann, K.A. et al., In vivo administration of CD4-specific monoclonal antibody: Effect on provirus load in rhesus monkeys chronically infected with the simian immunodeficiency virus of macaques. *AIDS Res Hum Retroviruses* 1995, 11(4), 517-525.
Rieber, E.P. et al., Monoclonal CD4 antibodies after accidental HIV infection. *Lancet* 1990, 336, 1007-1008.
Wang, C.Y. et al., Postexposure immunoprophylaxis of primary isolates by an antibody to HIV receptor complex. *Proc. Nat. Acad. Sci. USA* 1999, 96, 10367-10372.

(Continued)

*Primary Examiner*—Bruce Campell
*Assistant Examiner*—Agnieszka Boesen
(74) *Attorney, Agent, or Firm*—Morgan & Finnegan, LLP

(57) ABSTRACT

This invention is directed to deimmunized antibodies that are useful as immunotherapeutic drugs against Human Immunodeficiency Virus (HIV) and CD4-mediated autoimmune disorders. More specifically, antibodies expressed by clones, Clone 7 containing the recombinant genes B4DIVHv1/VK1CHO#7, Clone 16 containing the recombinant genes B4DIVHv1/VK1#16, and clone 21 containing the recombinant genes B4DIVHv1/VK1#21, are derived from mouse monoclonal B4 antibody (mAb B4). The antibodies were produced by removing particular murine determinants recognized as foreign by the human immune system. These recombinant antibodies were generated by the chimerization and deimmunization of the Fv region of mouse monoclonal antibody (mAb) B4. For improved safety, the coding sequence may further be mutated to express an aglycosylated $IgG_1$ antibody that is unable to bind complement. The deimmunized antibodies retain the specificity of the murine mAb B4 for a receptor complex involving CD4 on the surface of the host T cells, and retain the characteristic ability of mAb B4 to neutralize primary isolates of HIV.

**7 Claims, 18 Draw

OTHER PUBLICATIONS

Morrison, S.L. et al., Chimeric human antibody molecules: mouse antigen-binding domains with human constant region domains. *Proc Nat Acad Sci* USA 1984, 81(21), 6851-6855.

Reichmann, L. et al., Reshaping human antibodies. *Nature* 1988, 332, 323-327.

Co, M.S. et al., Humanized antibodies for antiviral therapy. *Proc Nat Aca Sci* USA 1991, 88, 2869-2873.

Adair, F. Immunogenicity—The last hurdle for clinically successful therapeutic antibodies. *BioPharm* 2000, (October), 42-46.

Padlan, E.A. A possible procedure for reducing the immunogenicity of antibody variable domains while preserving their ligand-binding properties. *Mol Immunol* 1991, 28(4-5), 489-498.

Altuvia, Y., Schueler, O. & Margalit, H. Ranking potential binding peptides to MHC molecules by a computational threading approach. *J Mol Biol* 1995, 249(2), 244-250.

Stiegler, G. et al., Antiviral activity of the neutralizing antibodies 2F5 and 2G12 in asymptomatic HIV-1-infected humans: a phase I evaluation. *AIDS* 2002, 16, 2019-2025.

Hofmann-Lehmann, R. et al., Postnatal passive immunization of neonatal macaques with a triple combination of human monoclonal antibodies against oral simian-human immunodeficiency virus challenge. *J. Virol* 2001, 75(16), 7470-7480.

Reimann, K.A. et al., A humanized form of a CD4-specific monoclonal antibody exhibits decreased antigenicity and prolonged plasma half-life in rhesus monkeys while retaining its unique biological and antiviral properties. *AIDS Res Hum Retroviruses* 1997, 13(11), 933-943.

Gen. Clinical trials update. *Genetic Engineering News* 2001, 21, 3.

Reiter, C. et al., Treatment of rheumatoid arthritis with monoclonal CD4 antibody M-T151. *Arthritis Rheum* 1991, 34(5), 525-536.

Van de Winkel, J. Antibody therapeutic approaches for inflammation. in *EULAR 2002 Annual European Congress of Rheumatology*, Stockholm, Sweden, 2002.

Kabat, E.A. The Kabat database of sequences of proteins of immunological interest. immuno.bme.nwu.edu.

Tomlinson, I.M. et al., The repertoire of human germline VH sequences reveals about fifty groups of VH segments with different hypervariable loops. *J. Mol. Biol.* 1992, 227, 776-798.

Cox, J.P.L. et al., A directory of human germ-line Vk segments reveals a strong bias in their usage. *Eur J Immunol* 1994, 24(4), 827-836.

Hieter, P.A. et al., Evolution of human immunoglobulin kappa J region genes. *J Biol Chem* 1982, 257(3), 1516-1522.

Hanson, C.V. et al., Application of a rapid microplaque assay for determination of human immunodeficiency virus neutralizing titers. *J Clin Microbiol* 1990, 28(9), 2030-2034.

Norderhaug, L. et al., Versatile vectors for transient and stable expression of recombinant antibody molecules in mammalian cells. *J Immunol Methods* 1997, 204(1), 77-87.

Mulligan, R.C. et al., Synthesis of rabbit beta-globin in cultured monkey kidney cells following infection with a SV40 beta-globin recombinant genome. *Nature* 1979, 277(5692), 108-114.

Mizushima, S. et al., pEF-BOS, a powerful mammalian expression vector. *Nucleic Acids Res* 1990, 18(17), 5322.

Page, M.J. & Sydenham, M.A. High level expression of the humanized monoclonal antibody Campath-1H in Chinese hamster ovary cells. *Boptechnology* 1991, 9(1), 64-68.

Bebbington, C.R. et al., High-level expression of a recombinant antibody from myeloma cells using a glutamine synthetase gene as an amplifiable selectable marker. *Biotechnology* 1992, 10(2), 169-175.

Kim, S.J. et al., Characterization of chimeric antibody producing CHO cells in the course of dihydrofolate reductase-mediated gene amplification and their stability in the absence of selective pressure. *Biotechnol Bioeng* 1998, 58(1), 73-84.

Tao, M.H. & Morrison, S.L. Studies of aglycosylated chimeric mouse-human IgG. Role of carbohydrate in the structure and effector functions mediated by the human IgG constant region. *J. Immunol.* 1989, 143(8), 2595-2601.

Wright, A. & Morrison, S.L. Effect of glycosylation on antibody function: implications for genetic engineering. *Trends Biotechnol* 1997, 15(1), 26-32.

Coloma, M.J. et al., The role of carbohydrate in the assembly and function of polymeric IgG. *Mol Immunol* 2000, 37(17), 1081-1090.

Leatherbarrow, R.J. et al, Effector functions of a monoclonal aglycosylated mouse IgG2a: binding and activation of complement C1 and interaction with human monocyte Fc receptor. *Mol Immunol* 1985, 22(4), 407-415.

Eloit, M. Risks of virus transmission associated with animal sera or substitutes and methods of control. *Dev Biol Stand* 1999, 99, 9-16.

Takahashi, N. et al., Structure of human immunoglobulin gamma genes: Implications for evolution of a gene family. *Cell* 1982, 29, 671-679.

Hieter, P.A. et al., Cloned human and mouse kappa immunoglobulin constant and J region genes conserve homology in functional segments. *Cell* 1980, 22(1 Pt 1), 197-207.

Mascola, J.R. et al., Human immunodeficiency virus type 1 neutralizing antibody serotyping using serum pools and an infectivity reduction assay. *AIDS Res Hum Retroiruses* 1996, 12(14), 1319-1328.

Remington's Pharmaceutical Sciences, Mack Publishing Company, Easton, Pa., 15th Edition 1975.

Ma, J.K-C., et al., Assembly of monoclonal antibodies with IgG1 and IgA heavy chain domains in transgenic tobacco plants. *Eur J Immunol* 1994, 24(1), 131-138.

Russell, D.A. Feasibility of antibody production in plants for human therapeutic use. *Curr Top Microbiol Imunol* 1999, 240, 119-138.

Motto, M. et al., Genetic manipulations of protein quality in maize grain. *Field Crops Researcch* 1996, 45, 37-48.

Menossi, M. et al., Improved analysis of promoter activity in biolistically transformed plant cells. *BopTechniques* 2000, 28(1), 54-58.

* cited by examiner

```
            10                  20                  30
 1  Q V Q L Q Q S G P E L V K P G A S V R M S C K A S G Y T F T   B4MoVH
 1  Q V Q L V Q S G P E   K K P G A S V K V S C K A S G Y T F T   B4DIVHv.1
 1  Q V Q L V Q S G A E V K K P G A S V K V S C K A S G Y T F T   B4DIVHv.2
 1  Q V Q L V Q S G A E V K K P G A S V K V S C K A S G Y T F T   B4DIVHv.3
 1  Q V Q L V Q S G A E V K K P G A S V K V S C K A S G Y T F T   B4DIVHv.4

40                  50                  60
31  D Y V I H W V K Q R T G Q G L E W I G E I Y P G S G S A Y S   B4MoVH
31  D Y V I H W V K Q A T G Q G L E W I G E I Y P G S G S A Y S   B4DIVHv.1
31  D Y V I H W V R Q A T G Q G L E W I G E I Y P G S G S A Y S   B4DIVHv.2
31  D Y V I H W V K Q A T G Q G L E W I G E I Y P G S G S A Y S   B4DIVHv.3
31  D Y V I H W V R Q A T G Q G L E W I G E I Y P G S G S A Y S   B4DIVHv.4

70                  80                  90
61  N A K F K D K A T L T A D K S S N T A Y M Q L S S L T S E D   B4MoVH
61  N A K F K D R V T M T A D K S S N T A Y M E L S S L T S D D   B4DIVHv.1
61  N A K F K D R V T I T A D K S T N T A Y M E L R S L R S D D   B4DIVHv.2
61  N A K F K D R V T I T A D K S T N T A Y M E L R S L R S D D   B4DIVHv.3
61  N S K F K D R V T I T A D K S T N T A Y M E L R S L R S D D   B4DIVHv.4

100                 110
91  S A V Y F C A R R G N G T G F A Y W G Q G T L V T V S A       B4MoVH    (SEQ ID NO. 2)
91  T A V Y F C A R R G N G T G F A Y W G Q G T L V T V S S       B4DIVHv.1 (SEQ ID NO. 5)
91  T A V Y F C A R R G N G T G F A Y W G Q G T L V T V S S       B4DIVHv.2 (SEQ ID NO. 6)
91  T A V Y F C A R R G N G T G F A Y W G Q G T L V T V S S       B4DIVHv.3 (SEQ ID NO. 7)
91  T A V Y F C A R R G N G T G F A Y W G Q G T L V T V S S       B4DIVHv.4 (SEQ ID NO. 8)
```

FIG. 5

```
                         10                  20                  30
   1    D I V L T Q S P A S L A V S L G Q R A T I S C K A G Q S V D    B4MoVK
   1    D I V L T Q S P A S L A V S L G Q R A T I T C K A G Q S V D    B4DIVKv.1
   1    D I V L T Q S P A S L A V S P G Q R A T I T C K A G Q S V D    B4DIVKv.2
   1    D I V L T Q S P A S L A V S P G Q R A T I T C K A G Q S V D    B4DIVKv.3

40                  50                  60
  31    Y D G D S Y M N W Y Q Q K P G Q P P K L L I Y V A S N L E S    B4MoVK
  31    Y D G D S Y M N W Y Q Q K P G Q P P K L L I Y V A S N L E S    B4DIVKv.1
  31    Y D G D S Y M N W Y Q Q K P G Q P P K L L I Y V A S N L E S    B4DIVKv.2
  31    Y D G D S Y M N W Y Q Q K P G Q P P K L L I Y V A S N L E S    B4DIVKv.3

70                  80                  90
  61    G I P A R F S G S G S G T D F T L N I H P V E E E D A A T Y    B4MoVK
  61    G I P A R F S G S G S G T D F T L N I H P V E E N D A A T Y    B4DIVKv.1
  61    G I P S R F S G S G S G T D F T L T I N P V E E N D T A T Y    B4DIVKv.2
  61    G I P S R F S G S G S G T D F T L T I N P V E E N D T A T Y    B4DIVKv.3

100                 110
  91    Y C Q Q S Y K D P L T F G A G T K L E L K                      B4MoVK       (SEQ. ID. No. 4)
  91    Y C Q Q S Y K D P L T F G Q G T K L E I K                      B4DIVKv.1    (SEQ. ID. No. 9)
  91    Y C Q Q S Y K D P L T F G Q G T K V E I K                      B4DIVKv.2    (SEQ. ID. No. 10)
  91    Y C Q Q S Y K D P L A F G P G T K V E I K                      B4DIVKv.3    (SEQ. ID. No. 11)
```

FIG. 6

```
            10         20         30         40         50
             |          |          |          |          |
  1 CAGGTTCAGC TGCAGCAGTC TGGACCTGAG CTGGTGAAGC CTGGGGCTTC  B4MoVH
  1 CAGGTTCAGC TGGTGCAGTC TGGACCTGAG CTGAAGAAGC CTGGGGCTTC  B4DIVHv.1
  1 CAGGTTCAGC TGGTGCAGTC TGGAGCTGAG GTGAAGAAGC CTGGGGCTTC  B4DIVHv.2
  1 CAGGTTCAGC TGGTGCAGTC TGGAGCTGAG GTGAAGAAGC CTGGGGCTTC  B4DIVHv.3
  1 CAGGTTCAGC TGGTGCAGTC TGGAGCTGAG GTGAAGAAGC CTGGGGCTTC  B4DIVHv.4

60         70         80         90        100
             |          |          |          |          |
 51 AGTGAGGATG TCCTGCAAGG CTTCTGGATA CACATTCACT GACTATGTTA  B4MoVH
 51 AGTGAAGGTG TCCTGCAAGG CTTCTGGATA CACATTCACT GACTATGTTA  B4DIVHv.1
 51 AGTGAAGGTG TCCTGCAAGG CTTCTGGATA CACATTCACT GACTATGTTA  B4DIVHv.2
 51 AGTGAAGGTG TCCTGCAAGG CTTCTGGATA CACATTCACT GACTATGTTA  B4DIVHv.3
 51 AGTGAAGGTG TCCTGCAAGG CTTCTGGATA CACATTCACT GACTATGTTA  B4DIVHv.4

110        120        130        140        150
             |          |          |          |          |
101 TACACTGGGT GAAGCAGAGA ACTGGACAGG GCCTTGAGTG GATTGGAGAG  B4MoVH
101 TACACTGGGT GAAGCAGGCG ACTGGACAGG GCCTTGAGTG GATTGGAGAG  B4DIVHv.1
101 TACACTGGGT GAGGCAGGCG ACTGGACAGG GCCTTGAGTG GATTGGAGAG  B4DIVHv.2
101 TACACTGGGT GAAGCAGGCG ACTGGACAGG GCCTTGAGTG GATTGGAGAG  B4DIVHv.3
101 TACACTGGGT GCGGCAGGCG ACTGGACAGG GCCTTGAGTG GATTGGAGAG  B4DIVHv.4

160        170        180        190        200
             |          |          |          |          |
151 ATTTATCCTG GAAGTGGTAG TGCTTACTCC AATGCGAAGT TCAAGGACAA  B4MoVH
151 ATTTATCCTG GAAGTGGTAG TGCTTACTCC AATGCGAAGT TCAAGGACAG  B4DIVHv.1
151 ATTTATCCTG GAAGTGGTAG TGCTTACTCC AATGCCAAGT TCAAGGACAG  B4DIVHv.2
151 ATTTATCCTG GAAGTGGTAG TGCTTACTCC AATGCGAAGT TCAAGGACAG  B4DIVHv.3
151 ATTTATCCTG GAAGTGGTAG TGCTTACTCC AATTCGAAGT TCAAGGACAG  B4DIVHv.4

210        220        230        240        250
             |          |          |          |          |
201 GGCCACACTG ACTGCAGACA AATCCTCCAA CACAGCCTAC ATGCAGCTCA  B4MoVH
201 GGTGACAATG ACTGCAGACA AATCCTCCAA CACAGCCTAC ATGGAGCTCA  B4DIVHv.1
201 GGTGACAATT ACTGCAGACA AATCCACAAA CACAGCCTAC ATGGAGCTCA  B4DIVHv.2
201 GGTGACAATT ACTGCAGACA AATCCACAAA CACAGCCTAC ATGGAGCTCA  B4DIVHv.3
201 GGTGACAATT ACTGCAGACA AATCCACAAA CACAGCCTAC ATGGAGCTCA  B4DIVHv.4

260        270        280        290        300
             |          |          |          |          |
251 GCAGTCTGAC ATCTGAGGAC TCTGCGGTCT ATTTCTGTGC AAGAAGAGGG  B4MoVH
251 GCAGTCTGAC ATCTGACGAC ACAGCGGTCT ATTTCTGTGC AAGAAGAGGG  B4DIVHv.1
251 GGAGTCTGAG GTCTGACGAC ACAGCGGTCT ATTTCTGTGC AAGAAGAGGG  B4DIVHv.2
251 GGAGTCTGAG GTCTGACGAC ACAGCGGTCT ATTTCTGTGC AAGAAGAGGG  B4DIVHv.3
251 GGAGTCTGAG GTCTGACGAC ACAGCGGTCT ATTTCTGTGC AAGAAGAGGG  B4DIVHv.4

310        320        330        340        350
             |          |          |          |          |
301 AATGGTACCG GGTTTGCTTA CTGGGGCCAA GGGACTCTGG TCACTGTCTC  B4MoVH
301 AATGGTACCG GGTTTGCTTA CTGGGGCCAA GGGACTCTGG TCACTGTCTC  B4DIVHv.1
301 AATGGTACCG GGTTTGCTTA CTGGGGCCAA GGGACTCTGG TCACTGTCTC  B4DIVHv.2
301 AATGGTACCG GGTTTGCTTA CTGGGGCCAA GGGACTCTGG TCACTGTCTC  B4DIVHv.3
301 AATGGTACCG GGTTTGCTTA CTGGGGCCAA GGGACTCTGG TCACTGTCTC  B4DIVHv.4

351 TGCA   B4MoVH      (SEQ ID NO:1)
351 TTCT   B4DIVHv.1   (SEQ ID NO:12)
351 TTCT   B4DIVHv.2   (SEQ ID NO:13)
351 TTCT   B4DIVHv.3   (SEQ ID NO:14)
351 TTCT   B4DIVHv.4   (SEQ ID NO:15)
```

FIG. 7

```
          10         20         30         40
           |          |          |          |
1   GACATTGTGC TGACCCAATC TCCAGCTTCT TTGGCTGTGT  B4MoVK
1   GACATTGTGC TGACCCAATC TCCAGCTTCT TTGGCTGTGT  B4DIVKv.1
1   GACATTGTGC TGACCCAATC TCCAGCTTCT TTGGCTGTGT  B4DIVKv.2
1   GACATTGTGC TGACCCAATC TCCAGCTTCT TTGGCTGTGT  B4DIVKv.3
          50         60         70         80
           |          |          |          |
41  CTCTAGGGCA GAGGGCCACC ATCTCCTGCA AGGCCGGCCA  B4MoVK
41  CTCTAGGGCA GAGGGCCACC ATCACCTGCA AGGCCGGCCA  B4DIVKv.1
41  CTCCAGGGCA GAGGGCCACC ATCACCTGCA AGGCCGGCCA  B4DIVKv.2
41  CTCCAGGGCA GAGGGCCACC ATCACCTGCA AGGCCGGCCA  B4DIVKv.3
          90        100        110        120
           |          |          |          |
81  AAGTGTTGAT TATGATGGTG ATAGTTATAT GAACTGGTAC  B4MoVK
81  AAGTGTTGAT TATGATGGTG ATAGTTATAT GAACTGGTAC  B4DIVKv.1
81  AAGTGTTGAT TATGATGGTG ATAGTTATAT GAACTGGTAC  B4DIVKv.2
81  AAGTGTTGAT TATGATGGTG ATAGTTATAT GAACTGGTAC  B4DIVKv.3
         130        140        150        160
           |          |          |          |
121 CAACAGAAAC CAGGACAGCC ACCCAAACTC CTCATCTATG  B4MoVK
121 CAACAGAAAC CAGGACAGCC ACCCAAACTC CTCATCTATG  B4DIVKv.1
121 CAACAGAAAC CAGGACAGCC ACCCAAACTC CTCATCTATG  B4DIVKv.2
121 CAACAGAAAC CAGGACAGCC ACCCAAACTC CTCATCTATG  B4DIVKv.3
         170        180        190        200
           |          |          |          |
161 TTGCATCCAA TCTAGAATCT GGGATCCCAG CCAGGTTTAG  B4MoVK
161 TTGCATCCAA TCTAGAATCT GGCATCCCAG CCAGGTTTAG  B4DIVKv.1
161 TTGCATCCAA TCTAGAATCT GGGATCCCAA GTAGGTTTAG  B4DIVKv.2
161 TTGCATCCAA TCTAGAATCT GGGATCCCAA GTAGGTTTAG  B4DIVKv.3
         210        220        230        240
           |          |          |          |
201 TGGCAGTGGG TCTGGGACAG ACTTCACCCT CAACATCCAT  B4MoVK
201 TGGCAGTGGG TCTGGGACAG ACTTCACCCT CAACATCCAT  B4DIVKv.1
201 TGGCAGTGGG TCTGGGACAG ACTTCACCCT CACAATCAAC  B4DIVKv.2
201 TGGCAGTGGG TCTGGGACAG ACTTCACCCT CACAATCAAC  B4DIVKv.3
         250        260        270        280
           |          |          |          |
241 CCTGTGGAGG AGGAGGATGC TGCAACCTAT TACTGTCAGC  B4MoVK
241 CCTGTGGAGG AGAACGATGC TGCAACCTAT TACTGTCAGC  B4DIVKv.1
241 CCTGTGGAGG AGAACGATAC CGCAACCTAT TACTGTCAGC  B4DIVKv.2
241 CCTGTGGAGG AGAACGATAC CGCAACCTAT TACTGTCAGC  B4DIVKv.3
         290        300        310        320
           |          |          |          |
281 AAAGTTATAA GGATCCGCTC ACGTTCGGTG CTGGGACCAA  B4MoVK
281 AAAGTTATAA GGACCCGCTC ACGTTCGGTC AGGGGACCAA  B4DIVKv.1
281 AAAGTTATAA GGATCCGCTC ACTTTCGGTC AGGGGACCAA  B4DIVKv.2
281 AAAGTTATAA GGATCCGCTC GCGTTCGGTC CGGGGACCAA  B4DIVKv.3
         330
           |
321 GCTGGAGCTG AAA        B4MoVK      (SEQ ID NO:3)
321 GCTGGAGATC AAA        B4DIVKv.1   (SEQ ID NO:16)
321 GGTGGAGATC AAA        B4DIVKv.2   (SEQ ID NO:17)
321 GGTGGAGATC AAA        B4DIVKv.3   (SEQ ID NO:18)
```

FIG. 8 cDNA and Amino Acid Sequences
for the CDRs of murine mAb B4
and Clones #16, 21, 7, $V_H$ CDRs CDR1
$nt_{76-105}$ GGATACACATTCACTGACTATGTTATACAC  (SEQ ID NO:19)
$AA_{26-35}$ GYTFTDYVIH  (SEQ ID NO:20)

CDR2
$nt_{148-198}$GAGATTTATCCTGGAAGTGGTAGTGCTTACTCCAATGCGAAGTTCAAGGAC
                                                     (SEQ ID NO:21)
$AA_{50-66}$ EIYPGSGSAYSNAKFKD  (SEQ ID NO:22)

CDR3
$nt_{295-321}$AGAGGGAATGGTACCGGGTTTGCTTAC  (SEQ ID NO:23)
$AA_{99-108}$ RGNGTGFAYW  (SEQ ID NO:24)

$V_K$ CDRs

CDR1
$nt_{70-114}$ AAGGCCGGCCAAAGTGTTGATTATGATGGTGATAGTTATATGAAC
                                                  (SEQ ID NO:25)
$AA_{24-38}$ KAGQSVDYDGDSYMN  (SEQ ID NO:26)

CDR2
$nt_{160-180}$  GTTGCATCCAATCTAGAATCT  (SEQ ID NO:27)
$AA_{54-60}$ VASNLES  (SEQ ID NO:28)

CDR3
$nt_{277-303}$  CAGCAAAGTTATAAGGACCCGCTCACG  (SEQ ID NO:29)
$AA_{93-101}$ QQSYKDPLT  (SEQ ID NO:30)

*At $nt_{294}$ of murine B4, it is Thymidine, in clones #7, #16, and #21, $nt_{294}$ was inadvertently changed to Cytosine.

FIG 18

SEQUENCE LISTING

<160> NUMBER OF SEQ ID NOS: 30

<210> SEQ ID NO 1
<211> LENGTH: 354
<212> TYPE: DNA
<213> ORGANISM: mouse

<400> SEQUENCE: 1

```
caggttcagc tgcagcagtc tggacctgag ctggtgaagc ctggggcttc agtgaggatg      60
tcctgcaagg cttctggata cacattcact gactatgtta tacactgggt gaagcagaga     120
actggacagg gccttgagtg gattggagag atttatcctg gaagtggtag tgcttactcc     180
aatgcgaagt tcaaggacaa ggccacactg actgcagaca atcctccaa cacagcctac     240
```

```
atgcagctca gcagtctgac atctgaggac tctgcggtct atttctgtgc aagaagaggg      300
aatggtaccg ggtttgctta ctggggccaa gggactctgg tcactgtctc tgca            354
```

<210> SEQ ID NO 2
<211> LENGTH: 118
<212> TYPE: PRT
<213> ORGANISM: mouse

<400> SEQUENCE: 2

```
Gln Val Gln Leu Gln Gln Ser Gly Pro Glu Leu Val Lys Pro Gly Ala
1               5                   10                  15

Ser Val Arg Met Ser Cys Lys Ala Ser Gly Tyr Thr Phe Thr Asp Tyr
            20                  25                  30

Val Ile His Trp Val Lys Gln Arg Thr Gly Gln Gly Leu Glu Trp Ile
        35                  40                  45

Gly Glu Ile Tyr Pro Gly Ser Gly Ser Ala Tyr Ser Asn Ala Lys Phe
    50                  55                  60

Lys Asp Lys Ala Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Phe Cys
                85                  90                  95

Ala Arg Arg Gly Asn Gly Thr Gly Phe Ala Tyr Trp Gly Gln Gly Thr
            100                 105                 110

Leu Val Thr Val Ser Ala
        115
```

<210> SEQ ID NO 3
<211> LENGTH: 333
<212> TYPE: DNA
<213> ORGANISM: mouse

<400> SEQUENCE: 3

```
gacattgtgc tgacccaatc tccagcttct ttggctgtgt ctctagggca gagggccacc       60
atctcctgca aggccggcca aagtgttgat tatgatggtg atagttatat gaactggtac      120
caacagaaac caggacagcc acccaaactc ctcatctatg ttgcatccaa tctagaatct      180
gggatcccag ccaggtttag tggcagtggg tctgggacag acttcaccct caacatccat      240
cctgtggagg aggaggatgc tgcaacctat tactgtcagc aaagttataa ggatccgctc      300
acgttcggtg ctgggaccaa gctggagctg aaa                                    333
```

<210> SEQ ID NO 4
<211> LENGTH: 111
<212> TYPE: PRT
<213> ORGANISM: mouse

<400> SEQUENCE: 4

```
Asp Ile Val Leu Thr Gln Ser Pro Ala Ser Leu Ala Val Ser Leu Gly
1               5                   10                  15

Gln Arg Ala Thr Ile Ser Cys Lys Ala Gly Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Val Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80
```

```
Pro Val Glu Glu Glu Asp Ala Ala Thr Tyr Tyr Cys Gln Gln Ser Tyr
                85                  90                  95

Lys Asp Pro Leu Thr Phe Gly Ala Gly Thr Lys Leu Glu Leu Lys
            100                 105                 110

<210> SEQ ID NO 5
<211> LENGTH: 118
<212> TYPE: PRT
<213> ORGANISM: mouse

<400> SEQUENCE: 5

Gln Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Val Ile His Trp Val Lys Gln Ala Thr Gly Gln Gly Leu Glu Trp Ile
        35                  40                  45

Gly Glu Ile Tyr Pro Gly Ser Gly Ser Ala Tyr Ser Asn Ala Lys Phe
    50                  55                  60

Lys Asp Arg Val Thr Met Thr Ala Asp Lys Ser Ser Asn Thr Ala Tyr
65                  70                  75                  80

Met Glu Leu Ser Ser Leu Thr Ser Asp Asp Thr Ala Val Tyr Phe Cys
                85                  90                  95

Ala Arg Arg Gly Asn Gly Thr Gly Phe Ala Tyr Trp Gly Gln Gly Thr
            100                 105                 110

Leu Val Thr Val Ser Ser
        115

<210> SEQ ID NO 6
<211> LENGTH: 118
<212> TYPE: PRT
<213> ORGANISM: mouse

<400> SEQUENCE: 6

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Val Ile His Trp Val Arg Gln Ala Thr Gly Gln Gly Leu Glu Trp Ile
        35                  40                  45

Gly Glu Ile Tyr Pro Gly Ser Gly Ser Ala Tyr Ser Asn Ala Lys Phe
    50                  55                  60

Lys Asp Arg Val Thr Ile Thr Ala Asp Lys Ser Thr Asn Thr Ala Tyr
65                  70                  75                  80

Met Glu Leu Arg Ser Leu Arg Ser Asp Asp Thr Ala Val Tyr Phe Cys
                85                  90                  95

Ala Arg Arg Gly Asn Gly Thr Gly Phe Ala Tyr Trp Gly Gln Gly Thr
            100                 105                 110

Leu Val Thr Val Ser Ser
        115

<210> SEQ ID NO 7
<211> LENGTH: 118
<212> TYPE: PRT
<213> ORGANISM: mouse

<400> SEQUENCE: 7
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Val Ile His Trp Val Lys Gln Ala Thr Gly Gln Gly Leu Glu Trp Ile
        35                  40                  45

Gly Glu Ile Tyr Pro Gly Ser Gly Ser Ala Tyr Ser Asn Ala Lys Phe
    50                  55                  60

Lys Asp Arg Val Thr Ile Thr Ala Asp Lys Ser Thr Asn Thr Ala Tyr
65                  70                  75                  80

Met Glu Leu Arg Ser Leu Arg Ser Asp Asp Thr Ala Val Tyr Phe Cys
                85                  90                  95

Ala Arg Arg Gly Asn Gly Thr Gly Phe Ala Tyr Trp Gly Gln Gly Thr
            100                 105                 110

Leu Val Thr Val Ser Ser
        115

<210> SEQ ID NO 8
<211> LENGTH: 118
<212> TYPE: PRT
<213> ORGANISM: mouse

<400> SEQUENCE: 8

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Val Ile His Trp Val Arg Gln Ala Thr Gly Gln Gly Leu Glu Trp Ile
        35                  40                  45

Gly Glu Ile Tyr Pro Gly Ser Gly Ser Ala Tyr Ser Asn Ser Lys Phe
    50                  55                  60

Lys Asp Arg Val Thr Ile Thr Ala Asp Lys Ser Thr Asn Thr Ala Tyr
65                  70                  75                  80

Met Glu Leu Arg Ser Leu Arg Ser Asp Asp Thr Ala Val Tyr Phe Cys
                85                  90                  95

Ala Arg Arg Gly Asn Gly Thr Gly Phe Ala Tyr Trp Gly Gln Gly Thr
            100                 105                 110

Leu Val Thr Val Ser Ser
        115

<210> SEQ ID NO 9
<211> LENGTH: 111
<212> TYPE: PRT
<213> ORGANISM: mouse

<400> SEQUENCE: 9

Asp Ile Val Leu Thr Gln Ser Pro Ala Ser Leu Ala Val Ser Leu Gly
1               5                   10                  15

Gln Arg Ala Thr Ile Thr Cys Lys Ala Gly Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Val Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80
```

```
Pro Val Glu Glu Asn Asp Ala Ala Thr Tyr Tyr Cys Gln Gln Ser Tyr
                85                  90                  95
Lys Asp Pro Leu Thr Phe Gly Gln Gly Thr Lys Leu Glu Ile Lys
            100                 105                 110
```

<210> SEQ ID NO 10
<211> LENGTH: 111
<212> TYPE: PRT
<213> ORGANISM: mouse

<400> SEQUENCE: 10

```
Asp Ile Val Leu Thr Gln Ser Pro Ala Ser Leu Ala Val Ser Pro Gly
1               5                   10                  15
Gln Arg Ala Thr Ile Thr Cys Lys Ala Gly Gln Ser Val Asp Tyr Asp
                20                  25                  30
Gly Asp Ser Tyr Met Asn Trp Tyr Gln Gln Lys Pro Gly Gln Pro Pro
            35                  40                  45
Lys Leu Leu Ile Tyr Val Ala Ser Asn Leu Glu Ser Gly Ile Pro Ser
        50                  55                  60
Arg Phe Ser Gly Ser Gly Ser Gly Thr Asp Phe Thr Leu Thr Ile Asn
65                  70                  75                  80
Pro Val Glu Glu Asn Asp Thr Ala Thr Tyr Tyr Cys Gln Gln Ser Tyr
                85                  90                  95
Lys Asp Pro Leu Thr Phe Gly Gln Gly Thr Lys Val Glu Ile Lys
            100                 105                 110
```

<210> SEQ ID NO 11
<211> LENGTH: 111
<212> TYPE: PRT
<213> ORGANISM: mouse

<400> SEQUENCE: 11

```
Asp Ile Val Leu Thr Gln Ser Pro Ala Ser Leu Ala Val Ser Pro Gly
1               5                   10                  15
Gln Arg Ala Thr Ile Thr Cys Lys Ala Gly Gln Ser Val Asp Tyr Asp
                20                  25                  30
Gly Asp Ser Tyr Met Asn Trp Tyr Gln Gln Lys Pro Gly Gln Pro Pro
            35                  40                  45
Lys Leu Leu Ile Tyr Val Ala Ser Asn Leu Glu Ser Gly Ile Pro Ser
        50                  55                  60
Arg Phe Ser Gly Ser Gly Ser Gly Thr Asp Phe Thr Leu Thr Ile Asn
65                  70                  75                  80
Pro Val Glu Glu Asn Asp Thr Ala Thr Tyr Tyr Cys Gln Gln Ser Tyr
                85                  90                  95
Lys Asp Pro Leu Ala Phe Gly Pro Gly Thr Lys Val Glu Ile Lys
            100                 105                 110
```

<210> SEQ ID NO 12
<211> LENGTH: 354
<212> TYPE: DNA
<213> ORGANISM: mouse

<400> SEQUENCE: 12

```
caggttcagc tggtgcagtc tggacctgag ctgaagaagc ctggggcttc agtgaaggtg      60
tcctgcaagg cttctggata cacattcact gactatgtta tacactgggt gaagcaggcg     120
actggacagg gccttgagtg gattggagag atttatcctg aagtggtag tgcttactcc      180
aatgcgaagt tcaaggacag ggtgacaatg actgcagaca atcctccaa cacagcctac     240
```

```
atggagctca gcagtctgac atctgacgac acagcggtct atttctgtgc aagaagaggg      300
aatggtaccg ggtttgctta ctggggccaa gggactctgg tcactgtctc ttct            354
```

<210> SEQ ID NO 13
<211> LENGTH: 354
<212> TYPE: DNA
<213> ORGANISM: mouse

<400> SEQUENCE: 13

```
caggttcagc tggtgcagtc tggagctgag gtgaagaagc ctggggcttc agtgaaggtg       60
tcctgcaagg cttctggata cacattcact gactatgtta tacactgggt gaggcaggcg      120
actggacagg gccttgagtg gattggagag atttatcctg aagtggtag tgcttactcc       180 aatgccaagt tcaaggacag ggtgacaatt actgcagaca atccacaaa cacagcctac       240 atggagctca ggagtctgag gtctgacgac acagcggtct atttctgtgc aagaagaggg      300
aatggtaccg ggtttgctta ctggggccaa gggactctgg tcactgtctc ttct            354
```

<210> SEQ ID NO 14
<211> LENGTH: 354
<212> TYPE: DNA
<213> ORGANISM: mouse

<400> SEQUENCE: 14

```
caggttcagc tggtgcagtc tggagctgag gtgaagaagc ctggggcttc agtgaaggtg       60
tcctgcaagg cttctggata cacattcact gactatgtta tacactgggt gaagcaggcg      120
actggacagg gccttgagtg gattggagag atttatcctg aagtggtag tgcttactcc       180 aatgcgaagt tcaaggacag ggtgacaatt actgcagaca atccacaaa cacagcctac       240 atggagctca ggagtctgag gtctgacgac acagcggtct atttctgtgc aagaagaggg      300
aatggtaccg ggtttgctta ctggggccaa gggactctgg tcactgtctc ttct            354
```

<210> SEQ ID NO 15
<211> LENGTH: 354
<212> TYPE: DNA
<213> ORGANISM: mouse

<400> SEQUENCE: 15

```
caggttcagc tggtgcagtc tggagctgag gtgaagaagc ctggggcttc agtgaaggtg       60
tcctgcaagg cttctggata cacattcact gactatgtta tacactgggt gcggcaggcg      120
actggacagg gccttgagtg gattggagag atttatcctg aagtggtag tgcttactcc       180 aattcgaagt tcaaggacag ggtgacaatt actgcagaca atccacaaa cacagcctac       240 atggagctca ggagtctgag gtctgacgac acagcggtct atttctgtgc aagaagaggg      300
aatggtaccg ggtttgctta ctggggccaa gggactctgg tcactgtctc ttct            354
```

<210> SEQ ID NO 16
<211> LENGTH: 333
<212> TYPE: DNA
<213> ORGANISM: mouse

<400> SEQUENCE: 16

```
gacattgtgc tgacccaatc tccagcttct ttggctgtgt ctctagggca gagggccacc       60
atcacctgca aggccggcca aagtgttgat tatgatggtg atagttatat gaactggtac      120
caacagaaac caggacagcc acccaaactc ctcatctatg ttgcatccaa tctagaatct      180
```

```
ggcatcccag ccaggtttag tggcagtggg tctgggacag acttcaccct caacatccat      240
cctgtggagg agaacgatgc tgcaacctat tactgtcagc aaagttataa ggacccgctc      300
acgttcggtc aggggaccaa gctggagatc aaa                                   333
```

<210> SEQ ID NO 17
<211> LENGTH: 333
<212> TYPE: DNA
<213> ORGANISM: mouse

<400> SEQUENCE: 17

```
gacattgtgc tgacccaatc tccagcttct ttggctgtgt ctccagggca gagggccacc       60
atcacctgca aggccggcca aagtgttgat tatgatggtg atagttatat gaactggtac      120
caacagaaac caggacagcc acccaaactc ctcatctatg ttgcatccaa tctagaatct      180
gggatcccaa gtaggtttag tggcagtggg tctgggacag acttcaccct cacaatcaac      240
cctgtggagg agaacgatac cgcaacctat tactgtcagc aaagttataa ggatccgctc      300
actttcggtc aggggaccaa ggtggagatc aaa                                   333
```

<210> SEQ ID NO 18
<211> LENGTH: 333
<212> TYPE: DNA
<213> ORGANISM: mouse

<400> SEQUENCE: 18

```
gacattgtgc tgacccaatc tccagcttct ttggctgtgt ctccagggca gagggccacc       60
atcacctgca aggccggcca aagtgttgat tatgatggtg atagttatat gaactggtac      120
caacagaaac caggacagcc acccaaactc ctcatctatg ttgcatccaa tctagaatct      180
gggatcccaa gtaggtttag tggcagtggg tctgggacag acttcaccct cacaatcaac      240
cctgtggagg agaacgatac cgcaacctat tactgtcagc aaagttataa ggatccgctc      300
gcgttcggtc cggggaccaa ggtggagatc aaa                                   333
```

<210> SEQ ID NO 19
<211> LENGTH: 30
<212> TYPE: DNA
<213> ORGANISM: mouse

<400> SEQUENCE: 19

```
ggatacacat tcactgacta tgttatacac                                        30
```

<210> SEQ ID NO 20
<211> LENGTH: 10
<212> TYPE: PRT
<213> ORGANISM: mouse

<400> SEQUENCE: 20

Gly Tyr Thr Phe Thr Asp Tyr Val Ile His
1               5                   10

<210> SEQ ID NO 21
<211> LENGTH: 51
<212> TYPE: DNA
<213> ORGANISM: mouse

<400> SEQUENCE: 21

```
gagatttatc ctggaagtgg tagtgcttac tccaatgcga agttcaagga c                51
```

<210> SEQ ID NO 22

```
<211> LENGTH: 17
<212> TYPE: PRT
<213> ORGANISM: mouse

<400> SEQUENCE: 22

Glu Ile Tyr Pro Gly Ser Gly Ser Ala Tyr Ser Asn Ala Lys Phe Lys
1               5                   10                  15
Asp

<210> SEQ ID NO 23
<211> LENGTH: 27
<212> TYPE: DNA
<213> ORGANISM: mouse

<400> SEQUENCE: 23
agagggaatg gtaccgggtt tgcttac                                          27

<210> SEQ ID NO 24
<211> LENGTH: 10
<212> TYPE: PRT
<213> ORGANISM: mouse

<400> SEQUENCE: 24

Arg Gly Asn Gly Thr Gly Phe Ala Tyr Trp
1               5                   10

<210> SEQ ID NO 25
<211> LENGTH: 45
<212> TYPE: DNA
<213> ORGANISM: mouse

<400> SEQUENCE: 25
aaggccggcc aaagtgttga ttatgatggt gatagttata tgaac                      45

<210> SEQ ID NO 26
<211> LENGTH: 15
<212> TYPE: PRT
<213> ORGANISM: mouse

<400> SEQUENCE: 26

Lys Ala Gly Gln Ser Val Asp Tyr Asp Gly Asp Ser Tyr Met Asn
1               5                   10                  15

<210> SEQ ID NO 27
<211> LENGTH: 21
<212> TYPE: DNA
<213> ORGANISM: mouse

<400> SEQUENCE: 27
gttgcatcca atctagaatc t                                                21

<210> SEQ ID NO 28
<211> LENGTH: 7
<212> TYPE: PRT
<213> ORGANISM: mouse

<400> SEQUENCE: 28

Val Ala Ser Asn Leu Glu Ser
1               5

<210> SEQ ID NO 29
<211> LENGTH: 27
<212> TYPE: DNA
<213> ORGANISM: mouse
```

```
<400> SEQUENCE: 29
cagcaaagtt ataaggaccc gctcacg                                            27

<210> SEQ ID NO 30
<211> LENGTH: 9
<212> TYPE: PRT
<213> ORGANISM: mouse

<400> SEQUENCE: 30

Gln Gln Ser Tyr Lys Asp Pro Leu Thr
1               5
```

DESIGNED DEIMMUNIZED MONOCLONAL ANTIBODIES FOR PROTECTION AGAINST HIV EXPOSURE AND TREATMENT OF HIV INFECTION

BACKGROUND OF THE INVENTION

Notwithstanding intensive research for a vaccine in the 20 years since the initial discovery of HIV as the causative agent of Acquired Immunodeficiency Syndrome (AIDS) and 18 years since the molecular cloning and characterization of the AIDS virus, major obstacles remain for HIV immunotherapy development. These hurdles include the hypervariability of HIV type 1 (HIV-1, the major HIV type), the multiple routes and/or modes of virus transmission, and a lack of understanding of the immune responses necessary for inhibition of HIV.

In a review by Moore et al. [1], it is reported that antibodies generated against variable exposed epitopes have effective neutralizing activity only against autologous viruses and isolates with closely-related envelope proteins (env). Further, the monoclonal antibodies (mAbs) that recognize more conserved regions of env, targets of better immunotherapeutic potential, almost never strongly neutralize multiple primary isolates. The basic knowledge needed for achievement of broad anti-viral antibodies remains so enigmatic that the field of HIV vaccinology is now focused on approaches which offer at best only a hope for partial protection against disease [2].

Primary isolates of HIV-1 are obtained by limited cultivation of patient peripheral blood mononuclear cells (PBMCs) or patient plasma with uninfected PBMCs. They closely resemble HIV field strains responsible for human infection [3]. Primary isolates are readily distinguished from commonly used laboratory-adapted T-tropic viruses such as IIIb/LAI, SF2, and MN, which have been reproduced and are well-adapted to grow in human T-lymphoid cell lines.

First, most primary HIV-1 isolates are M-tropic. They do not readily grow in cultured T cell lines, but rather they are monocyte or macrophage-tropic with the ability to infect primary T cells [4]. Second, primary isolates are highly resistant to in vitro neutralization by recombinant soluble forms of the viral receptor protein CD4 (rsCD4) and require 200-2700 times more rsCD4 than laboratory strains for comparable neutralization [5]. Third, primary isolates are also resistant to neutralizing antibodies elicited by the use of gp120 vaccines [6].

Primary isolates include both syncytium-inducing isolates (SI) and non-syncytium-inducing (NSI) isolates in PBMC culture. Most SI primary isolates will replicate in the highly HIV-sensitive T cell line MT2, but few can replicate in the less permissive transformed T cell lines CEM or H9 that are commonly used to culture laboratory-adapted isolates. Non-syncytium-inducing (NSI) primary isolates can only be cultured in the primary T cells from peripheral blood.

There was mistaken early optimism for efficacious antibody responses to recombinant HIV-1 envelope subunit vaccines (e.g., gp120 and gp160 vaccine products). The vaccinee sera from clinical trials of experimental envelope-based vaccines often were capable of neutralizing laboratory isolates of HIV-1 in vitro [7,8]. At the time, the basic differences between laboratory-adapted and primary isolates were not yet understood. This optimism was soon shaken when the antibodies in the vaccinee sera were found to be largely ineffective in neutralizing HIV-1 primary patient isolates [6,9].

Early optimism for effective vaccine-induced antibodies also was mistakenly brought about by studies of inactivated virus preparations of Simian Immunodeficiency Virus (SIV).

Due to similarities between HIV-1 and SIV in morphology, genetic organization, infection and disease processes, SIV infection in rhesus monkeys seemed to be an excellent model to explore different AIDS vaccine and anti-HIV antibody strategies. Early studies in the SIV model showed that inactivated preparations of SIV grown on human T cell lines and formulated in adjuvant can protect macaques from infection after experimental inoculation with highly infectious, pathogenic variants of human cell-grown SIV [10]. Unexpectedly, this protection was lost when an SIV stock grown on homologous monkey cells was used for the challenge of immunized animals.

Later immunization studies with monkey cell-grown SIV and uninfected human cells showed that protection from infection in those early SIV studies probably resulted from the stimulation of immune responses to xenogeneic human host cell proteins rather than to virus-encoded antigens [11]. Passive immunization experiments involving SIV suggested that certain anti-cell antibodies may contribute to protection against SIV infection in the absence of cell-mediated immunity [12].

The mechanism by which anti-cell antibodies provides protective immunity to retroviral challenge has not been delineated. One mode of action for such protection may be mediated by blocking the CD4 binding site for immunodeficiency viruses on immune system cells. Anti-CD4 monoclonal antibodies have long been known to block infection in a manner that is dependent on the CD4 epitope, not the virus strain [13,14]. Monoclonal antibody 5A8, which recognizes CD4 domain 2, had shown therapeutic efficacy in SIV-infected macaques [15]. Anti-CD4 monoclonal antibodies Leu3A and P1, which recognize the CDR2-like loop in CD4 domain 1, blocked infection of cell cultures by primary isolates [5,14].

Anti-CD4 antibodies inhibit virus-to-cell or infected cell-to-uninfected cell transmission of both SI and NSI strains of HIV 1 [16]. The surface of host T cells appears to have a host cell antigen complex associated with CD4 that facilitates viral binding and entry and acts as a target for protective anti-cell antibodies [17,18].

Murine monoclonal antibody B4 (mAb B4) [17,18] is an anti-cell antibody that was developed by using CD4-expressing T lymphocytes, such as peripheral blood mononuclear T cells, thymocytes, splenocytes and leukemia or lymphoma-derived T cell lines, e.g., HPB-ALL or SUP-T1, as the immunogen. MAb B4 was characterized by its ability to neutralize primary isolates of HIV-1 and related immunodeficiency viruses both in vitro and in vivo Specifically, mAb B4 acts by blocking the binding of HIV to CD4+ host cells. It is an entry inhibitor, a new class of anti-retroviral drugs for the treatment of HIV infection, providing potentially an orthogonal therapy to highly active antiretroviral therapy (HAART).

MAb B4 was directed against a host cell surface antigen complex comprising CD4 protein in association with domains from chemokine receptors. MAb B4 recognizes CD4 by a CD4 extracellular region binding site on the CDR2-like loop in domain 1. This is not coincident with the binding site for Leu3A. U.S. Pat. No. 5,912,176 discloses strong evidence that this B4 antibody has broad neutralizing activities against primary isolates from all clades of HIV-1 and primary isolates of HIV type 2 (HIV-2) and SIV. When monoclonal antibodies with specificities for various cell surface antigens were mixed, only those mixtures including mAb B4 displayed strong neutralizing activity for HIV-1 B-clade primary field isolates. (Column 24, lines 1-10; Column 47, lines 5-10.) Furthermore, in neutralization assays on primary isolates of HIV-2 (i.e., HIV-$2_{ROD}$) and SIV strains, mAb B4 exhibited strong neutralization for all strains whereas no comparative result was shown by the anti-N-terminal V3 MN antibody previously shown to be effective on laboratory-adapted HIV-1 MN. (Column 45, lines 19-35.)

Additional studies of mAb B4 neutralizing activity for HIV-1 and primary isolates of HIV-2 and SIV demonstrate its efficacy in mice, chimpanzees, and rhesus macaques. For example, the administration of mAb B4 after infectious challenge, interrupted the infection by PBL-grown HIV-1 of hu-peripheral blood leukocyte (PBL)-severe combined immuno-deficient mice [18]. Also, the administration of mAb B4 in chimpanzees after infectious challenge totally interrupted the infection by chimp-adapted HIV-1 [18]. Furthermore, following challenge with a dose of $SIV_{mac251}$ that caused persistent infection in rhesus macaques, passive immunization of these animals with a modest dose (4 mg/kg) of mAb B4 is found to effectively protect 75 percent of the monkeys from infection by an SIV primary isolate, (U.S. Pat. No. 5,912,176, Column 50, lines 15-22.)

The requirement for CD4 as the receptor for efficient HIV infection suggests that the CD4 molecule may be a good target for immunotherapy by anti-cell antibodies like mAb B4, as long as there is not undue immunomodulatory effects.

However, the use of murine monoclonal antibodies like mAb B4 for therapeutic and in vivo diagnostic applications in man has been found to be limited by immune responses made by patients to the murine antibodies. The development of "HAMA" (human anti-murine antibody) responses in patients has limited the ability of murine antibodies to reach their antigenic targets and reduced the effectiveness of the antibodies in therapeutic use.

Antibody humanization technologies have been devised to reduce the HAMA response. For example, murine antibodies can be converted to chimeric mouse/human antibodies wherein the entire DNA coding sequences for the variable domains of the mouse immunoglobulin are joined to the regions encoding the human constant domains [19]. Mouse DNA sequences can be further reduced for better humanization by complementarity determining region (CDR) grafting. A rat Fv region was reshaped for use in human immunotherapy by excising the DNA coding regions for the six CDRs from the rat heavy and light chain variable regions and grafting them into the coding regions for the framework sequences of the human heavy and light chains. The reshaped variable region coding sequence was then assembled onto human constant domains [20].

However, chimeric and engrafted antibodies in which the variable region or CDRs remain murine may still be immunogenic. Moreover, grafting CDRs onto unrelated frameworks may lead to loss in affinity of the humanized antibody. Consequently, humanization of murine monoclonal antibodies was further applied by employing sequence homology and molecular modeling. These methods were used to select more homologous human frameworks for the murine CDRs that retain high-binding affinity and minimize the use of murine residues to those essential for contact [21].

Since the purpose for humanizing therapeutic murine antibodies is to reduce immunogenicity in human recipients, deimmunization is a useful alternative process. Deimmunization reduces the immunogenicity of rodent variable domains in humans simply by removing epitopes from the variable domains of rodent antibodies that are likely to be immunogenic in humans.

In practice, an effective primary immune response against a therapeutic antibody involves: the processing of foreign proteins, presentation of antigenic peptides by MHC class II molecules (T-cell epitopes), and then stimulation of helper T-cells. In turn, these helper T-cells trigger and enhance the B cell production of antibodies which bind to the therapeutic antibodies. Furthermore, if one or more sequences within a therapeutic antibody (B-cell epitopes) is bound by immature B-cell surface immunoglobulins (sIg) in the presence of suitable cytokines, the B-cell can be stimulated to differentiate and proliferate to provide soluble forms of the original sIg. These soluble forms of the original sIg can complex with the therapeutic antibody to limit its effectiveness and facilitate its clearance from the patient. Therefore, to avoid a primary immune response against the therapeutic mAb, both the B- and T-cell epitopes within the antibody that are potentially antigenic in humans should be eliminated or modified.

Without either the B or T-cell response, the primary immunogenic response to a therapeutic antibody is likely to be muted or absent. The DeImmunisation® technology developed by Biovation Ltd. (Aberdeen, UK) [22,23] focuses on the removal of potentially immunogenic B cell and T cell epitopes. This method was applied in the present invention to deimmunize mAb B4. Removal of B cell epitopes is achieved by the 'veneering' of surface residues with substituent amino acids [24]. Removal of the T cell epitopes is achieved following the identification of such epitopes from the variable regions of the therapeutic antibodies whereby the sequences of the variable region can be analyzed by the presence of MHC class II-binding motifs by a 3-dimensional "peptide threading" method [25]. The antibody constant regions of the murine antibody are replaced by the human antibody constant regions in the final deimmunized antibody by chimerization [19].

Passive immune therapy with human, humanized or deimmunized antibody may play an important role in the treatment or prevention of HIV infection. Human anti-HIV monoclonal antibodies 2F5 and 2G12 are known to neutralize primary isolates of HIV and have been used for studies in HIV-infected humans. Transient reduction in viral loads and transient increases in CD4+ T cells were observed [26]. These antibodies also have been studied in a non-human primate model for immune prophylaxis against mother-to-child transmission. Whether the antibodies were administered through the placenta by intravenous infusion into the mother prenatally or by direct infusion into rhesus macaque neonates following birth, the neonates were protected from challenge by infectious simian/human immunodeficiency virus (SHIV). The authors concluded that immunoprophylaxis with a combination of anti-viral monoclonal antibodies is a promising approach to prevent maternal HIV transmission in humans [27]. Passive immunity has also been proposed for use in post-exposure prophylaxis against HIV in the event of accidental exposure to HIV [16,18].

Since certain CD4-specific monoclonal antibodies can efficiently block infection of lymphocytes and macrophages by primary isolates of HIV-1 with a breadth higher than that of neutralizing anti-HIV antibodies [5,18,28], receptor-directed monoclonal antibodies like mAb B4 may be even better candidates for prophylaxis against HIV exposure and for therapy of HIV infection. Toward this purpose, monoclonal antibody 5A8 (mAb 5A8) has been previously reconfigured into a humanized $IgG_4$ antibody by a CDR engraftment method [28]. As an $IgG_4$ isotype, the humanized mAb 5A8 lacks a glycosylation site on the CH2 domain that is associated with complement fixation. This feature should improve the safety profile of similar antibodies by making it less likely to cause depletion of $CD4^+$ lymphocytes in patients. Humanized 5A8 has been entered into a clinical trial in HIV-infected patients [29].

Additionally, anti-CD4 monoclonal antibodies have shown clinical benefit in humans with rheumatoid arthritis [30]. A human monoclonal antibody, HuMax-CD4, has been entered into clinical trial for treatment of rheumatoid arthritis and psoriasis [31]. These applications demonstrate the potential usefulness of deimmunized antibodies such as those derived from B4 antibodies as immunotherapeutic drugs against Human Immunodeficiency Virus (HIV) and CD4-mediated autoimmune disorders.

REFERENCES CITED

1. Moore, J. P., Parren, P. W. H. I. & Burton, D. R. Genetic subtypes, humoral immunity, and human immunodeficiency virus type 1 vaccine development. *J. Virol.* 2001, 75(13), 5721-5729.
2. Moore, J. P. AIDS vaccines: On the trail of two trials. *Nature* 2002, 415, 365-366.
3. Sawyer, L. S. W., Wrin, M. T., Crawford-Miksza, L. et al. Neutralization sensitivity of human immunodeficiency virus type 1 is determined in part by the cell in which the virus is propagated. *J. Virol.* 1994, 68(3), 1342-1349.
4. Cheng-Mayer, C., Seto, D., Tateno, M. & Levy, J. A. Biologic features of HIV-1 that correlate with virulence in the host. *Science* 1988, 240, 80-82.
5. Daar, E. S., Li, X. L., Moudgil, T. & Ho, D. D. High concentrations of recombinant soluble CD4 are required to neutralize primary human immunodeficiency virus type 1 isolates. *Proc. Nat. Acad. Sci. USA* 1990, 87(17), 6574-6578.
6. Mascola, J. R., Snyder, S. W., Weislow, O. S. et al. Immunization with envelope subunit vaccine products elicits neutralizing antibodies against laboratory-adapted but not primary isolates of human immunodeficiency virus type 1. The National Institute of Allergy and Infectious Diseases AIDS Vaccine Evaluation Group. *J Infect Dis* 1996, 173 (2), 340-348.
7. Belshe, R. B., Graham, B. S., Keefer, M. C. et al. Neutralizing antibodies to HIV-1 in seronegative volunteers immunized with recombinant gp120 from the MN strain of HIV-1. NIAID AIDS Vaccine Clinical Trials Network. *JAMA* 1994, 272(6), 475-480.
8. Keefer, M. C., Graham, B. S., Belshe, R. B. et al. Studies of high doses of a human immunodeficiency virus type 1 recombinant glycoprotein 160 candidate vaccine in HIV type 1-seronegative humans. The AIDS Vaccine Clinical Trials Network. *AIDS Res Hum Retroviruses* 1994, 10(12), 1713-1723.
9. Hanson, C. V. Measuring vaccine-induced HIV neutralization: Report of a workshop. *AIDS Res Hum Retroviruses* 1994, 10(6), 645-648.
10. Desrosiers, R. C., Wyand, M. S., Kodama, T. et al. Vaccine protection against simian immunodeficiency virus infection. *Proc Nat Acad Sci USA* 1989, 86, 6353-6357.
11. Stott, E. J. Anti-cell antibody in macaques. *Nature* 1991, 353(6343), 393.
12. Gardner, M., Rosenthal, A., Jennings, M., Yee, J., Antipa, L. & Robinson, E. J. Passive immunization of rhesus macaques against SIV infection and disease. *AIDS Res Hum Retroviruses* 1995, 11(7), 843-854.
13. Sattentau, Q. J., Dalgleish, A. G., Weiss, R. A. & Beverley, P. C. L. Epitopes of the CD4 antigen and HIV infection. *Science* 1986, 234, 1120-1123.
14. Jameson, B. D., Rao, P. E., Kong, L. L. et al. Location and chemical synthesis of a binding site for HIV-1 on the CD4 protein. *Science* 1988, 240, 1335-1339.
15. Reimann, K. A., Cate, R. L., Wu, Y. et al. In vivo administration of CD4-specific monoclonal antibody: Effect on provirus load in rhesus monkeys chronically infected with the simian immunodeficiency virus of macaques. *AIDS Res Hum Retroviruses* 1995, 11(4), 517-525.
16. Rieber, E. P., Reiter, C., Gurtler, L., Deinhardt, F. & Riethmuller, G. Monoclonal CD4 antibodies after accidental HIV infection. *Lancet* 1990, 336, 1007-1008.
17. Wang, C. Y. Antibodies against a host cell antigen complex for pre and post exposure protection from infection by HIV. U.S. Pat. No. 5,912,176 1999.
18. Wang, C. Y., Sawyer, L. S. W., Murthy, K. K. et al. Postexposure immunoprophylaxis of primary isolates by an antibody to HIV receptor complex. *Proc. Nat. Acad. Sci. USA* 1999, 96, 10367-10372.
19. Morrison, S. L., Johnson, M. L., Herzenberg, L. A. & Oi, V. T. Chimeric human antibody molecules: mouse antigen-binding domains with human constant region domains. *Proc Nat Acad Sci USA* 1984, 81(21), 6851-6855.
20. Reichmann, L., Clark, M., Waldmann, H. & Winter, G. Reshaping human antibodies. *Nature* 1988, 332, 323-327.
21. Co, M. S., Deschamps, M., Whitley, R. J. & Queen, C. Humanized antibodies for antiviral therapy. *Proc Nat Acad Sci USA* 1991, 88, 2869-2873.
22. Carr, F. J., Carter, G., Hamilton, A. A. & Adair, F. S. Reducing immunogenicity of proteins—by modifying the amino acid sequence of the protein to eliminate potential epitopes for T-cells of a given species. International Patent Application WO9852976 1998.
23. Adair, F. Immunogenicity—The last hurdle for clinically successful therapeutic antibodies. *BioPharm.* 2000, (October), 42-46.
24. Padlan, E. A. A possible procedure for reducing the immunogenicity of antibody variable domains while preserving their ligand-binding properties. *Mol Immunol* 1991, 28(4-5), 489-498.
25. Altuvia, Y., Schueler, O. & Margalit, H. Ranking potential binding peptides to MHC molecules by a computational threading approach. *J Mol Biol* 1995, 249(2), 244-250.
26. Stiegler, G., Armbruster, C., Vcelar, B. et al. Antiviral activity of the neutralizing antibodies 2F5 and 2G12 in asymptomatic HIV-1-infected humans: a phase I evaluation. *AIDS* 2002, 16, 2019-2025.
27. Hofmann-Lehmann, R., Vlasak, J., Rasmussan, R. A. et al. Postnatal passive immunization of neonatal macaques with a triple combination of human monoclonal antibodies against oral simian-human immunodeficiency virus challenge. *J Virol* 2001, 75(16), 7470-7480.
28. Reimann, K. A., Lin, W., Bixler, S. et al. A humanized form of a CD4-specific monoclonal antibody exhibits decreased antigenicity and prolonged plasma half-life in rhesus monkeys while retaining its unique biological and antiviral properties. *AIDS Res Hum Retroviruses* 1997, 13(11), 933-943.
29. GEN. Clinical trials update. *Genetic Engineering News* 2001, 21, 3.
30. Reiter, C., Kakavand, B., Rieber, E. P., Schattenkirchner, M., Riethmuller, G. & Kruger, K. Treatment of rheumatoid arthritis with monoclonal CD4 antibody M-T151. *Arthritis Rheum* 1991, 34(5), 525-536.
31. Van de Winkel, J. Antibody therapeutic approaches for inflammation. in *EULAR* 2002 *Annual European Congress of Rheumatology*, Stockholm, Sweden, 2002.
32. Kabat, E. A. The Kabat database of sequences of proteins of immunological interest. immuno.bme.nwu.edu.
33. Tomlinson, I. M., Walter, G., Marks, J. D., Llewelyn, M. B. & Winter, G. The repertoire of human germline $V_H$ sequences reveals about fifty groups of $V_H$ segments with different hypervariable loops. *J. Mol. Biol.* 1992, 227, 776-798.

34. Cox, J. P. L., Tomlinson, I. M. & Winter, G. A directory of human germ-line Vk segments reveals a strong bias in their usage. *Eur J Immunol* 1994, 24(4), 827-836.

35. Hieter, P. A., Maizel, J. V. J. & Leder, P. Evolution of human immunoglobulin kappa J region genes. *J Biol Chem* 1982, 257(3), 1516-1522.

36. Hanson, C. V., Crawford-Miksza, L. & Sheppard, H.W. Application of a rapid microplaque assay for determination of human immunodeficiency virus neutralizing titers. *J Clin Microbiol* 1990, 28(9), 2030-2034.

37. Norderhaug, L., Olafsen, T., Michaelsen, T. E. & Sandlie, I. Versatile vectors for transient and stable expression of recombinant antibody molecules in mammalian cells. *J Immunol Methods* 1997, 204(1), 77-87.

38. Mulligan, R. C., Howard, B. H. & Berg, P. Synthesis of rabbit beta-globin in cultured monkey kidney cells following infection with a SV40 beta-globin recombinant genome. *Nature* 1979, 277(5692), 108-114.

39. Mizushima, S. & Nagata, S. pEF-BOS, a powerful mammalian expression vector. *Nucleic Acids Res* 1990, 18(17), 5322.

40. Page, M. J. & Sydenham, M. A. High level expression of the humanized monoclonal antibody Campath-1H in Chinese hamster ovary cells. *Biotechnology* 1991, 9(1), 64-68.

41. Bebbington, C. R., Renner, G., Thomson, S., King, D., Abrams, D. & Yarranton, G. T. High-level expression of a recombinant antibody from myeloma cells using a glutamine synthetase gene as an amplifiable selectable marker. *Biotechnology* 1992, 10(2), 169-175.

42. Kim, S. J., Kim, N. S., Ryu, C. J., Hong, H. J. & Lee, G. M. Characterization of chimeric antibody producing CHO cells in the course of dihydrofolate reductase-mediated gene amplification and their stability in the absence of selective pressure. *Biotechnol Bioeng* 1998, 58(1), 73-84.

43. Tao, M. H. & Morrison, S. L. Studies of aglycosylated chimeric mouse-human IgG. Role of carbohydrate in the structure and effector functions mediated by the human IgG constant region. *J. Immunol.* 1989, 143(8), 2595-2601.

44. Wright, A. & Morrison, S. L. Effect of glycosylation on antibody function: implications for genetic engineering. *Trends Biotechnol* 1997, 15(1), 26-32.

45. Coloma, M. J., Clift, A., Wims, L. & Morrison, S. L. The role of carbohydrate in the assembly and function of polymeric IgG. *Mol Immunol* 2000, 37(17), 1081-1090.

46. Leatherbarrow, R. J., Rademacher, T. W., Dwek, R. A. et al. Effector functions of a monoclonal aglycosylated mouse IgG2a: binding and activation of complement C1 and interaction with human monocyte Fc receptor. *Mol Immunol* 1985, 22(4), 407-415.

47. Eloit, M. Risks of virus transmission associated with animal sera or substitutes and methods of control. *Dev Biol Stand* 1999, 99, 9-16.

48. Takahashi, N., Ueda, S., Obata, M., Nikaido, T., Nakai, S. & Honjo, T. Structure of human immunoglobulin gamma genes: Implications for evolution of a gene family. *Cell* 1982, 29, 671-679.

49. Hieter, P. A., Max,. E. E., Seidman, J. D., Maizel, J. V. J. & Leder, P. Cloned human and mouse kappa immunoglobulin constant and J region genes conserve homology in functional segments. *Cell* 1980, 22(1 Pt 1), 197-207.

50. Mascola, J. R., Louder, M. K., Surman, S. R. et al. Human immunodeficiency virus type 1 neutralizing antibody serotyping using serum pools and an infectivity reduction assay. *AIDS Res Hum Retroviruses* 1996, 12(14), 1319-1328.

51. Remington's Pharmaceutical Sciences, Mack Publishing Company, Easton, Pa., 15th Edition 1975.

52. Ma, J. K-C., Lehner, T., Stabila, P., Fux, C. I. & Hiatt, A. Assembly of monoclonal antibodies with IgG1 and IgA heavy chain domains in transgenic tobacco plants. *Eur J Immunol* 1994, 24(1), 131-138.

53. Russell, D. A. Feasibility of antibody production in plants for human therapeutic use. *Curr Top Microbiol Immunol* 1999, 240, 119-138.

54. Motto, M., Hartings, H., Maddaloni, M., Lohmer, S., Salamini, F., Thompson, R. Genetic manipulations of protein quality in maize grain. *Field Crops Research* 1996, 45, 37-48.

55. Menossi, M., Puigdomenech, P., Martinez-Izquierdo, J. A. Improved analysis of promotor activity in biolistically transformed plant cells. *BioTechniques* 2000, 28(1), 54-58.

SUMMARY OF THE INVENTION

The present invention is directed to deimmunized antibodies derived from mouse monoclonal antibody B4 that are useful for immunotherapy against AIDS and other CD4-mediated disorders. The present invention is also directed to methods of treatment using the deimmunized antibodies. More particularly, antibodies expressed by clones #7, #16 and #21 containing the recombinant genes B4DIVHv1k/VK1#7, B4DIVHv1/VK1#16, and B4DIVHv1/VK1#21 are derived from mouse monoclonal B4 antibody (U.S. Pat. No. 5,912, 176, issued Jun. 15, 1999). Mouse monoclonal B4 antibody is characterized by its specificity for the HIV receptor complex on $CD4^+$ T cells and by its ability to neutralize in vitro and in vivo primary isolates of HIV and related immunodeficiency viruses [17,18].

The deimmunized recombinant antibodies were generated by a process that included expression from the fusion of the cDNA or polynucleotide encoding the Fv fragment of mAb B4 to the cDNA or polynucleotide for the human $IgG_1$ Fc fragment. The nucleotide sequence of the resulting chimeric genes with the murine Fv region was then deimmunized by directed mutagenesis to remove "foreign to human" B cell and T cell epitopes from the variable domains of the murine heavy ($V_H$) and κ ($V_κ$) chains so that it is suitable for treatment in human subjects. Four alternative cDNA or polynucleotide sequences are provided for the deimmunized $V_H$ chain and three for the deimmunized $V_κ$ chain. A deimmunized antibody was also engineered into an N-aglycosylated $IgG_1$ form by using site-directed mutagenesis to alter a glycosylation site so that it is unable to bind complement. Thus, the aglycosylated deimmunized antibody does not evoke complement-mediated lysis of bound $CD4^+$ cells.

These novel deimmunized antibodies retain the specificity and neutralization activities of the original murine monoclonal antibody.

These antibodies, expressed by NSO mouse myeloma cells and Chinese Hamster Ovary (CHO) cell clones, were adapted to serum-free medium for large-scale production for use in humans. The deimmunized antibodies may also be produced on a large scale in transgenic plants to reduce the cost. The antibodies of the invention may be used for prophylaxis of HIV exposure, for immunotherapy of HIV infection, and for immunotherapy of CD4-mediated autoimmune disorders such as rheumatoid arthritis.

BRIEF DESCRIPTION OF THE DRAWINGS

FIG. 5. Amino acid sequence comparisons for the murine B4 VH region, B4MoVH (SEQ ID NO.:2), and four alternative deimmunized VH regions, B4DIVHv.1 (SEQ ID NO:5), B4DIVHv.2 (SEQ ID NO:6), B4DIVHv.3 (SEQ ID NO:7), B4DIVHv.4 (SEQ ID NO:8). Positions where residues differ from that of B4MoVH (SEQ ID NO:2) are shown in boxes.

FIG. 6. Amino acid sequence comparisons for the murine B4 $V_κ$ region, B4MoVK (SEQ ID NO.: 4), and three alternative deimmunized $V_κ$ regions, B4DIVKv.1 (SEQ ID NO:9), B4DIVKv.2 (SEQ ID NO:10) and B4DIVK-v.3 (SEQ ID NO:11). Positions where residues differ from that of B4MoVK (SEQ ID NO:4) are shown in boxes.

FIG. 7. Nucleotide sequence comparisons for the murine B4 $V_H$ region, B4MoVH (SEQ ID NO:1), and four alternative deimmunized $V_H$ regions, B4DIVHv.1 (SEQ ID NO:12), B4DIVHv.2 (SEQ ID NO:13), B4DIVHv.3 (SEQ ID NO:14) and B4DIVHv.4 (SEQ ID NO:15). Positions where residues differ from that of B4MoVH (SEQ ID NO:1) are bolded and underlined.

FIG. 8. Nucleotide sequence comparisons for the murine B4 $V_κ$ region, B4MoVK (SEQ ID NO.: 3), and three alternative deimmunized $V_κ$ regions, B4DIVKv.1 (SEQ ID NO:16), B4DIVKv.2 (SEQ ID NO:17) and B4DIVKv.3 (SEQ ID NO:18). Positions where residues differ from that of B4MoVK (SEQ ID NO:3) are bolded and underlined.

FIG. 18 The cDNA and amino acid sequences for the CDRs of murine mAb B4 and clones #7, #16 and #21.

DETAILED DESCRIPTION OF THE INVENTION

The deimmunization of the Fv fragment of murine mAb B4 was achieved by the identification and elimination of potentially immunogenic murine T and B-cell epitopes. Removal of the T cell epitopes was achieved following the identification of such epitopes from the variable regions of the therapeutic antibodies. The amino acid sequences of the variable region were analyzed for the presence of MHC class II-binding motifs by a 3-dimensional "peptide threading" method [22,25]. Removal of at least one or all of the B cell epitopes from the variable region was achieved by the 'veneering' of surface residues where this will not interfere with antibody recognition [22,24]. The constant regions of the murine antibody ($C_H$ and $C_κ$) were entirely removed by replacement of the murine constant regions with human $IgG_1$ constant regions through the chimerization of the DNA sequence for the mAb B4 variable region with that for human $IgG_1$ constant regions.

Figure 1:
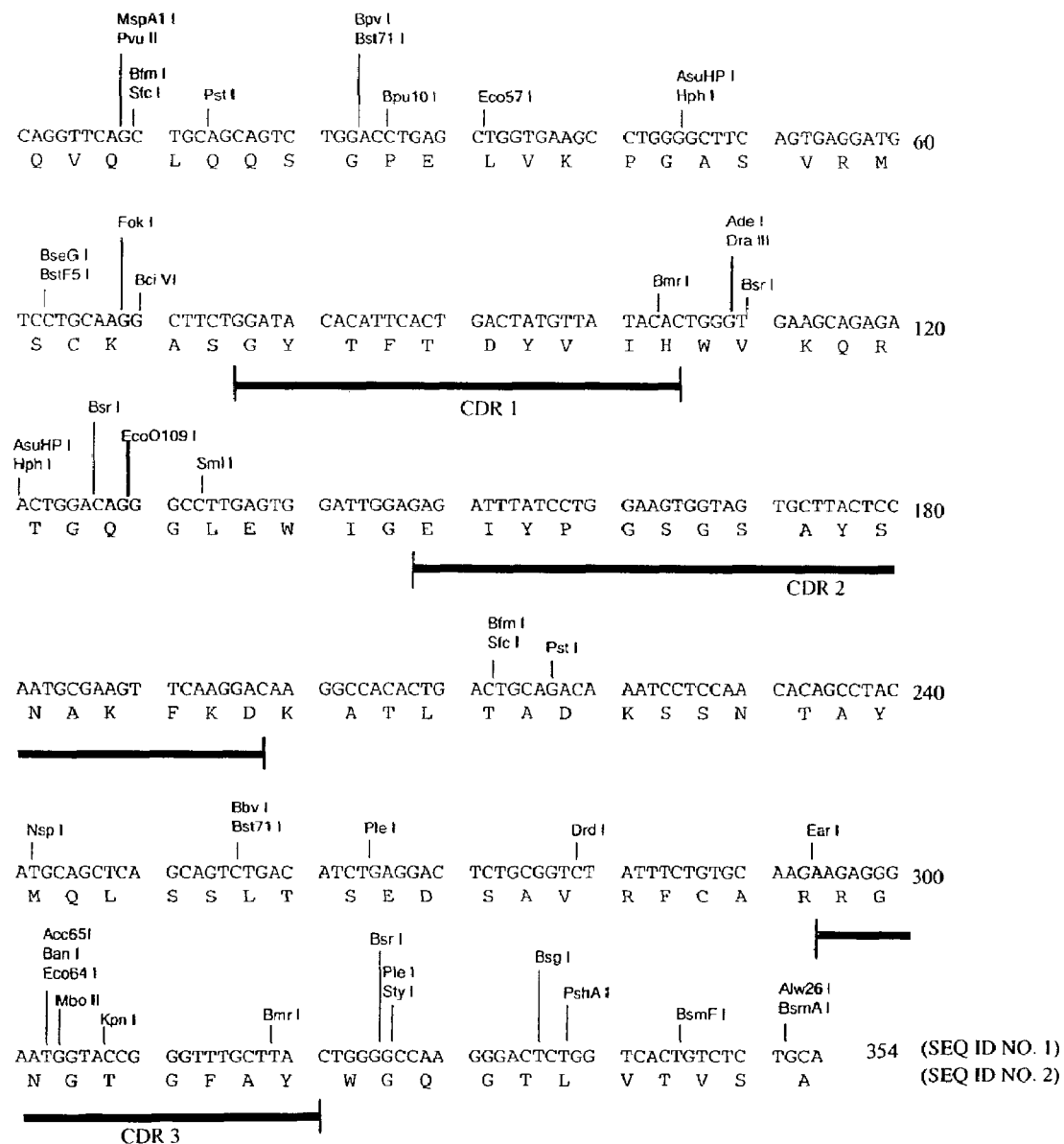
FIG. 1. DNA and amino acid sequences of the heavy chain of the murine monoclonal antibody B4 B4MoVH (SEQ ID NOS: 1 and 2) and restriction enzyme map.
Figure 2:
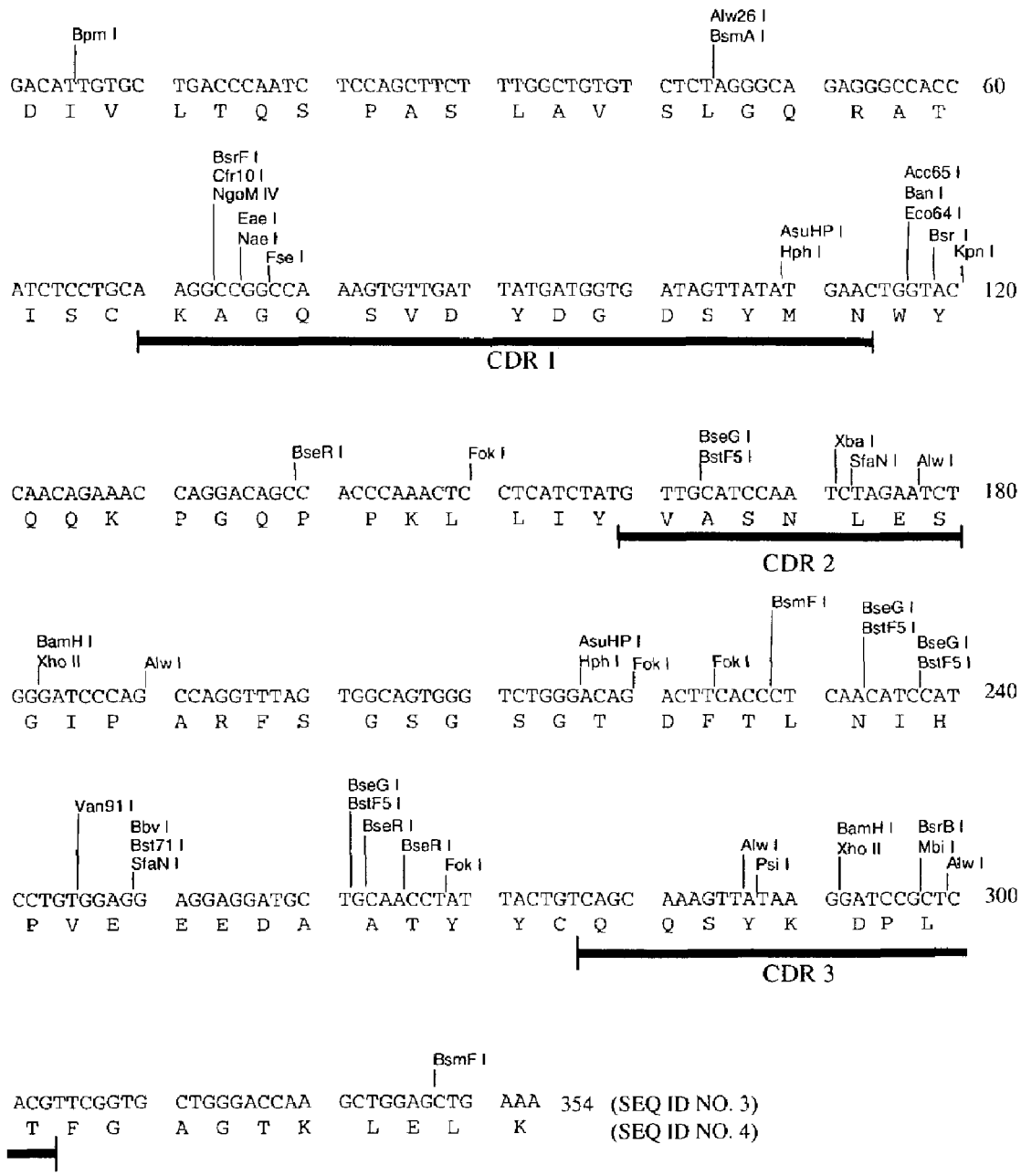
FIG. 2. DNA and amino acid sequences of the light (κ) chain of the murine monoclonal antibody B4 B4MoVK (SEQ ID NOS: 3 and 4) and restriction enzyme map.

Example 1 below describes in detail the recovery, cloning and sequencing of the DNA encoding the variable regions of the heavy and light chains of murine mAb B4. The DNA and amino acid sequences of the murine B4 $V_H$ are shown in FIG. 1. The DNA and amino acid sequences of the murine B4 $V_κ$ are shown in FIG. 2. The locations of the CDRs on both chains were determined by reference to other antibody sequences [32]. B4 $V_H$ and $V_κ$ can be respectively assigned to the Mouse Heavy Chains Subgroup V(B) and the Mouse Kappa Chains Subgroup III [32]. If desired, intermediate chimeric antibodies containing fully human constant regions and fully murine variable regions can be obtained as described in Example 2 herein. Confirmation that the correct variable regions were obtained was shown by the binding of the resulting chimeric antibody to recombinant soluble CD4 (rsCD4).

The cDNA or polynucleotide sequences encoding murine B4 $V_H$ and $V_κ$ were compared to the sequences of the directory of human germline $V_H$ [33] and $V_κ$ [34] sequences and also to human germline J region sequences [35]. The reference human framework selected for B4 $V_H$ was DP14 with human $J_H6$. The reference human framework selected for B4 $V_κ$ was B1. The J region sequence was human $J_κ2$.

Following identification of the reference human framework sequences, certain nucleotide sequences for non-identical amino acid residues within the B4 $V_H$ and $V_κ$ frameworks were changed to the corresponding nucleotide sequence in the human reference sequence. Residues which were considered to be critical for antibody structure and binding were excluded from this process and not altered. These include identifying the B4 $V_H$ and $V_κ$ complementarity determining regions (CDRs) listed as SEQ ID NOs:20, 22, 24, 26, 28 and 30 in FIG. 18. The CDR residues and those in the immediate framework neighborhood of the CDRs, such as those at the N-terminus for instance, were retained [24]. Other murine residues that were retained at this stage were largely non-surface, buried residues.

This process produced a sequence that is broadly similar to a 'veneered' antibody as the surface residues are mainly human and the buried residues are those in the original murine sequence. These sequences were then subjected to peptide threading to identify potential T cell epitopes, through analysis of binding to 18 different human MHC class II allotypes. Primary deimmunized $V_H$ and $V_\kappa$ sequences were defined (B4DIVHv.1, B4DIVKv.1). As generation of the primary deimmunized sequences requires a small number of nucleotide sequence substitutions that might affect the binding of the final deimmunized molecule, three other variant $V_H$s and two other $V_\kappa$s were designed. The comparative amino acid sequences of murine and deimmunized V regions are shown in FIG. 5 for for $V_H$ and FIG. 6 for $V_\kappa$. The comparative nucleotide sequences of the murine and deimmunized V regions are shown in FIG. 7 for $V_H$ and FIG. 8 for $V_\kappa$.

The method of constructing the nucleotide sequence fragment for the deimmunized variable regions including 5' flanking sequence, the leader signal peptide, leader intron and the murine immunoglobulin promoter, and 3' flanking sequence, the splice site and intron sequences is detailed in Example 3.

Once the deimmunized heavy and light chain V-region genes were constructed, they were respectively transferred to the expression vectors containing human $IgG_1$ $C_H$ or $C_\kappa$ regions. Markers for selection in mammalian cells (FIGS. 3 and 4) were also intoduced into the vectors. The recombinant vectors were then transfected into NSO cells. The expressed deimmunized antibodies were then purified from the culture media and were tested for binding to rsCD4 and for neutralizing activity against HIV-1.

Figure 16:
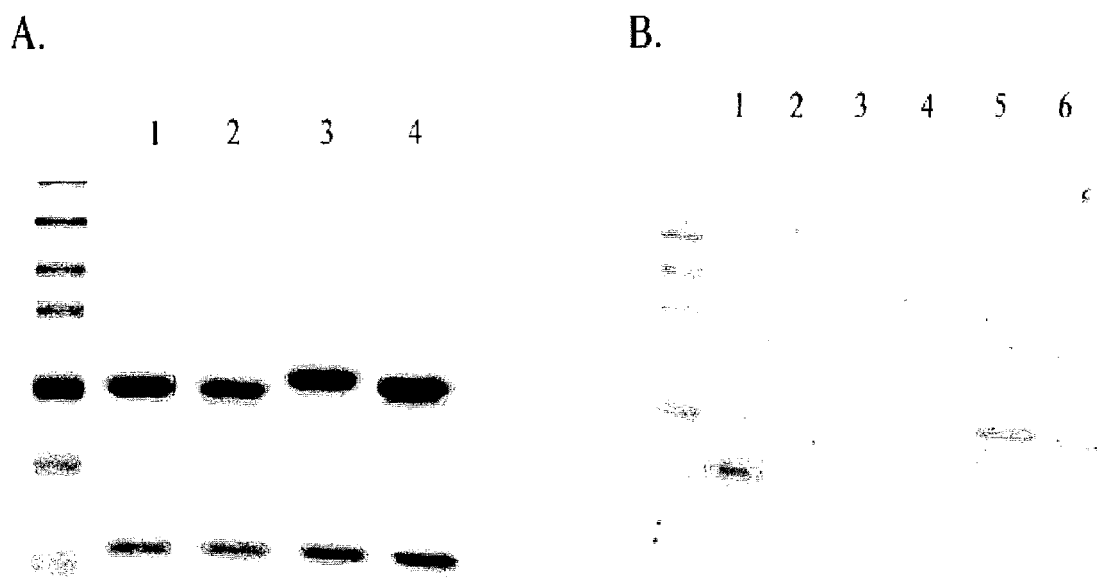
FIG. 16. SDS-PAGE analysis for glycosidase-mediated shifts in mobilities and reductions in intensities of Coomassie Blue staining.

The twelve variants of mAb B4 showed different binding affinities to rsCD4 by ELISA assay. The twelve variant B4 deimmunized antibodies also showed different neutralizing activities against SI primary isolates from HIV-1 subgroups A, B, C, D and E and T cell line isolate HIV-$1_{MN}$ by the MT-2 microplaque assay [36]. The comparisons of the four heavy chain variants (VHv.1-4), all combined with deimmunized .kappa chain version 1 (VKv.1), showed that the antibody having the version 1 heavy chain had high neutralizing activity against all of the HIV-1 primary isolates, with activities approaching that of murine mAb B4 for HIV-$1_{VL135}$, HIV-$1_{UG029}$ and HIV-$1_{TH036}$ (Table 1).

The deimmunized B4 antibodies were ineffective against the T cell line-adapted HIV-$1_{MN}$ virus as was the murine parent antibody. Deimmunized antibodies comprising κ chain versions 2 and 3 either were comparable or had lower neutralizing activities (Table 2). The comparisons of the 12 variants showed that the antibody having the DIVHv.1 heavy chain and DIVKv.1 had high neutralizing activity against all of the HIV-1 primary isolates, with activities against HIV-1 approaching that of murine mAb B4.

For the production of the present deimmunized B4 monoclonal antibodies, any appropriate expression system, including eukaryotic cells, for example, animal cells, such as established mammalian cell lines, or plant cells, may be used. Preferably, the present deimmunized antibodies are expressed in mammalian cells such as NSO cells or CHO cells. NSO , a non-immunoglobulin producing mouse myeloma can be obtained from the European Collection of Animal Cell Culture, Porton UK (ECACC no. 85110505). CHO cells lacking the enzyme dihydrofolate reductase ($CHOdhfr^-$) can be obtained from the American Type Culture Collection (ATCC no. CRL-9096).

For high-level expression of recombinant antibodies, dihydrofolate reductase (dhfr)-deficient CHO cells are one of the most widely used mamalian expression systems for gene amplification. Recombinant CHO cells are commonly used because the productivity of these cells has been found to increase with gene copy number and has been calculated to have specific antibody productivity as high as 100 $\mu g/10^6$ cells per day [42].

In such cases, a conventional promoter useful for expression in mammalian cells can be used. For example, a viral expression system including the human cytomegalovirus immediate early (CMV) promoter is preferred [37]. Alternatively, other promoters suitable for gene expression of the present invention in mammalian cells can be used. These promoters include viral promoters such as retrovirus, polyoma virus, adenovirus and simian virus 40 (SV40) or mammalian cell-derived promoters such as human elongation factor 1α promoter [38,39]. Immunoglobulin promoter could be used in lymphatic cells such as NSO cells. The vectors containing the Ig promoter, leader signal peptide, leader intron, the splice site, intron sequences and suitable restriction sites for the insertion of any variable region cassette were designed and constructed as described in Example 2. These vectors were expressed in NSO cells for convenient screening for expression of deimmunized antibodies by ELISA and bioactivity.

High level recombinant protein expression in mammalian cells can be obtained by selection of stable cell lines followed by amplification of transfected DNA. A recombinant gene can be co-amplified with a selection marker gene during DNA amplification. $CHOdhfr^-$ cells and the amplificable selection marker gene for dihydrofolate reductase (DHFR) can be used to establish cell lines that produce clinically useful amounts of product [40]. Alternatively, the glutamine synthetase (GS) gene also can be used as a dominant selection marker. Due to insufficient endogenous GS activity of myeloma and hybridoma cell lines, these cell lines have an absolute requirement for glutamine. Transfected GS gene is able to confer the ability to grow in an appropriate, glutamine free medium [41]. Preferably, the $CHOdfhr^-$ cells are used to express B4 deimmunized antibody, and the dhfr gene is used as the selection and amplification marker.

The plasmids for expression of antibody and DHFR in $CHOdhfr^-$ cells were constructed as described in Example 5. The expression levels of DHFR and antibody genes are amplified for greater production of deimmunized B4 antibodies by stepwise increases in methotrexate (MTX) concentrations [42].

Recombinant CHO (rCHO) cells with specific antibody productivity of 10-30 pg/cell/day were obtained through several rounds of selection in medium containing stepwise increases in MTX level.

Although expression of the deimmunized antibodies is preferably in mammalian cells, such as NSO or CHO cells, to reduce the cost of production on a large scale, expression in transgenic plants may also be employed. See Example 10.

All antibodies are glycoproteins. $IgG_1$ contains a biantennary complex N-linked carbohydrate within CH2 [43]. Presence of this carbohydrate is important for effector functions such as complement fixation and antigen-dependent-cellular-cytotoxicity (ADCC) which result in elimination of the target cell [44]. B4 antibody is targeted to the CD4 receptor complex and it may cause the destruction of $CD4^+$ cells and immunosuppression of $CD4^+$ cell function through the effector functions of $IgG_1$ that are responsible for binding complement. Therefore, an N-aglycosylated deimmunized B4 monoclonal antibody has the potential to be less depleting of $CD4^+$ cells and less immunotoxic than an N-glycosylated $IgG_1$ antibody. Removing the N-glycosylation site in the Fc region of $IgG_1$ by mutation has been shown to abolish the ability of $IgG_1$ to bind the human FcR1, to activate complement, and to bind C1 q [45].

Two general approaches have been used to remove carbohydrate: tunicamycin treatment of the antibody-producing cells to inhibit the attachment of carbohydrate precursor to asparagines [46], or removal of $Asn_{297}$ by mutation to another amino acid. The present deimmunized antibodies were modified by removal of the $Asn_{297}$ site for N-linked glycosylation. The AAC codon for $Asn_{297}$ of the heavy chain expression vector was mutated to the CAC codon for His by site-directed mutagenesis PCR. The N-aglycosylated deimmunized antibodies were expressed in CHO cells, and N-aglycosyated antibodies were secreted by these cells (FIG. 16).

The functional properties and safety feature of the deimmunized monoclonal antibodies are important considerations associated with their usage as human therapeutic drugs, and they need to be characterized. Within this context, they have been evaluated for their in vitro capabilities to: (1) neutralize HIV-1 viruses, (2) fix complement, and (3) stimulate human lymphocytes to elicit immune responses.

The HIV-1 neutralization activity of the deimmunized monoclonals derived from CHO clones as compared to the murine mAb B4 counterpart was assessed using the MT-2 microplaque assay [36]. The results of this study shown in Table 3 reveal that the deimmunized antibody DH1DK1CHO#21 expressed by Clone 21 exhibited virus neutralization capability comparable to the murine antibody produced by the B4 hybridoma. This was evident from the amount of these monoclonal antibodies required to achieve 50% neutralization of the representative viruses selected from the five clades (A to E) of HIV-1 tested. The aglycosylated deimmunized antibody DH1DK1CHO#7 had exhibited significantly enhanced neutralizing capability against the viruses 23135 from lade B, UG046 from clade D and TH036 from clade E as compared to the murine B4 antibody (Table 3).

Figure 17:
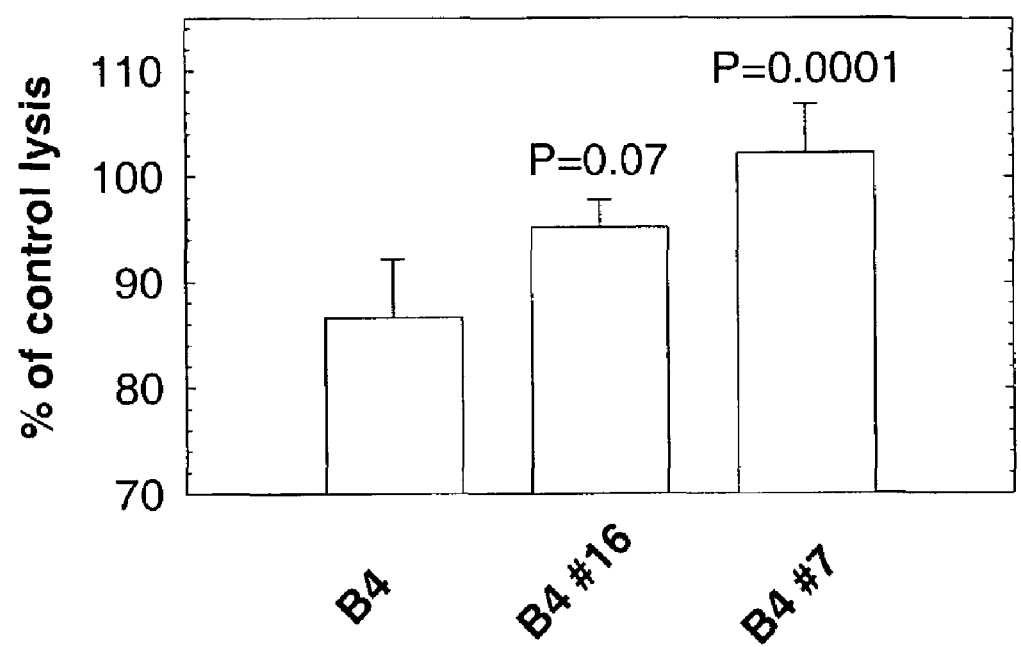
FIG. 17. Complement fixation tests. The P values for comparisons between murine mAb B4 and deimmunized B4 #16 and #7 were 0.07 and 0.0001, respectively, by Student's t-test.

A complement consumption assay was employed to evaluate the complement fixation property of the deimmunized antibodies as compared to their native counterpart, murine mAb B4 (Example 7). The results obtained from this assay showed that deimmunization of B4 had led to a reduction of the complement fixation property (FIG. 17). This was evident from the higher amount of complement remaining in the supernatant collected from the reaction mixture performed with the deimmunized antibodies in comparison to the reaction performed with the murine monoclonal. That result suggests that the deimmunized antibodies bound to the CD4 complex on human $CD4^+$ cells were less able to initiate complement fixation than the original murine antibody which more effectively fixed complement when bound to the CD4 cell surface complex. Thus, the supernatant assayed from the reaction mixture performed with murine B4 had contained less complement able to lyse the sensitized SRBC. The results obtained from this study means that the deimmunized antibodies DH1DK1CHO#7 and DH1DK1CHO#16 have greater safety than murine mAb B4 in view of their reduced capacities for fixing complement, and that the N-aglycosylated deimmunized antibody, as expected, has the least capacity for binding complement.

The immunogenicity of murine monoclonal antibodies in their application as human therapeutic drugs could lead to the generation of both human T and B cell responses directed against the therapeutic antibodies. The T cell responses elicited could result in the production of cytokines capable of modulating the immune responses the human subjects may be initiating against particular infectious agents or cancer at the time. A disturbance caused by the presence of murine antibody-induced cytokines may therefore result in the induction of imbalanced or even impaired immune responses required to fight off the invading pathogens or cancer.

The B cell responses elicited would generate human anti-mouse antibodies in the host. This would lead to the formation of antigen-antibody immune complexes and the deposit of these complexes in undesirable tissue sites to cause inflammation and/or pathological conditions in the human subject. In addition, the human anti-mouse antibodies would bind to the administered drug and reduce the effective concentration, thus preventing the therapeutic drug from reaching its desired targets, i.e., $CD4^+$ cells.

In view of the above considerations, we tested the immunogenicity of the deimmunized monoclonal antibodies and mAb B4 in an in vitro human peripheral blood mononuclear cell (PBMC) culture system (see Example 8). The results obtained from this study are shown in Table 4. It was found that the purified murine B4 antibody stimulated human PBMC to produce IL-10 and TNF-α; while IFN-γ and IL-2 generally accepted to be secreted by antigen-activated Th1 CD4 and another cytokine, IL-4, produced by Th2 CD4 cells, were not detected.

In contrast, the deimmunized antibodies DH1DK1CHO#16 and aglycosylated DH1DK1CHO#7 were both found to be non-immunogenic as judged by their failure to induce the human PBMC to secrete any of the 5 cytokines tested. These findings add to the safety value of these deimmunized monoclonal antibodies in their usage as therapeutic drugs.

The regulatory and the cost advantages of serum-free mammalian cell growth medium has been well established. The use of animal sera in cell culture processes brings along with it the potential for introduction of adventitious agents such as viruses and other transmissible agents (e.g., bovine spongiform encephalopathy) [47]. Additionally, the use of animal sera as a raw material impacts negatively on the cost of large-scale cell-culture processes. Finally, because protein biotherapeutics produced by mammalian cells are secreted into the medium, the use of serum-free medium greatly simplifies the development and robust execution of downstream protein purification processes.

The serum-dependent growth properties of rCHO cells require that cell line adaptation be carried out to obtain phenotypes appropriate for large-scale, serum-free, suspension culture-based manufacturing processes. The process described in Example 6 led to the successful adaptation of an rCHO clone for suspension growth and antibody expression in serum-free medium, with the production of deimmunized antibodies at a level equal to that of cells grown in monolayer cells in medium containing 10 fetal calf serum. The antibody produced in serum-free suspension culture had HIV-1 neutralization activity equal to those of antibodies secreted by monolayer cells cultured in medium containing 10% serum.

Collectively, these results strongly support the efficacy and safety of deimmunized antibodies as therapeutic drugs capable of reducing virus load in HIV-infected patients, and preventing establishment of infection following exposure.

The route(s) of administration useful in a particular application are apparent to one or ordinary skill in the art. Routes of administration of the antibodies include, but are not limited to, parenteral, and direct injection into an affected site. Parenteral routes of administration include but are not limited to intravenous, intramuscular, intraperitoneal and subcutaneous.

The present invention includes compositions of the deimmunized antibodies described above, suitable for parenteral administration including, but not limited to, pharmaceutically acceptable sterile isotonic solutions. Such solutions include, but are not limited to, saline and phosphate buffered saline for intravenous, intramuscular, intraperitoneal, or subcutaneous injection, or direct injection into a joint or other area.

In providing the deimmunized antibodies of the present invention to a recipient mammal, preferably a human, the dosage of administered antibodies will vary depending upon such factors as the mammal's age, weight, height, sex, general medical condition, previous medical history and the like. The determination of the optimum dosage and of the optimum route and frequency of administration is well within the knowledge of those skilled in the art. Similarly, dosages for other deimmunized antibodies within the scope of the present invention can be determined without excessive experimentation.

The deimmunized antibodies disclosed herein may be administered to a human patient, in a pharmaceutically acceptable dosage form, suitable for intravenous, subcutaneous or intramuscular administration. Such dosage forms encompass pharmaceutically acceptable carriers that are inherently nontoxic and nontherapeutic. Examples of such carriers include ion exchangers, alumina, aluminum stearate, lecithin, serum proteins, such as human serum albumin, buffer substances such as phosphates, glycine, mannitol, sorbic acid, hydrochloric acid, potassium sorbate, partial glyceride mixtures of saturated vegetable fatty acids, water, salts, or electrolytes such as protamine sulfate, disodium hydrogen phosphate, potassium dihydrogen phosphate, sodium chloride, sodium phosphate monobasic, sodium phosphate dibasic, dibasic sodium phosphate dihydrate, sodium hydroxide, zinc salts, colloidal silica, magnesium trisilicate, polyvinyl pyrrolidone, cellulose-based substances, and polyethylene glycol. The deimmunized antibodies will typically be formulated in such vehicles at a concentration of about 0.1 mg/ml to 100 mg/ml.

Pharmaceutical compositions may be prepared and formulated in dosage forms by methods known in the art; for example, see Remington's Pharmaceutical Sciences [51].

In general, it is desirable to provide the recipient with an initial candidate dosage of deimmunized antibodies which is in the range from about 1 to 100 mg/kg, preferably about 1 to 25 mg/kg, more preferably about 1 to 10 mg/kg, most preferably about 2 to 5 mg/kg of deimmunized antibody, whether, for example, by one or more separate administrations, or by continuous infusion. In general, the antibodies will be administered intravenously (IV) or intramuscularly (IM). For repeated administrations over several days or longer, depending on the condition, the treatment is repeated until a desired suppression of disease symptoms occurs or the desired improvement in the patient's condition is achieved. The dose may be readministered at intervals ranging from once a week to once every six months. The determination of the optimum dosage and of optimum route and frequency of administration is well within the knowledge of those skilled in the art. Similarly, dosages for other deimmunized antibodies within the scope of the present invention can be determined without excessive experimentation.

The deimmunized antibodies of the present invention may also be used in combination with antibodies with specificity for HIV such as antibodies to gp41 and gp120 of HIV. These include, but are not limited to, antibodies designated as 2F5, which is specific for gp41, and 2G12, which is specific for gp120, that are described by Hofmann-Lehmann, et al. [27].

A variety of procedures are shown in the examples below for illustrating the present invention and its utilization. These examples are for purpose of illustration only, and are not to be construed as limiting the scope of the invention.

EXAMPLE 1

Cloning and Characterization of the Murine mAb B4 Genes

1. Preparation of Total RNA

Total RNA was extracted from $5 \times 10^6$ hybridoma B4 cells by using the Promega (Madison, Wis.) SV40 Total RNA Isolation System (Cat. No. Z3100) according to the manufacturer's instructions.

2. Amplification of cDNAs Coding for Mouse Heavy Chain Variable Region ($V_H$) and Light Chain Variable Region (V)

Synthesis of the single stranded cDNA and amplification of cDNAs coding $V_H$ and $V_\kappa$ were done using GeneAmp® RNA PCR Kit (Perkin Elmer, Norwalk, Conn., part no. N808-0017), according to the manufacturer's instructions.

Briefly, the single stranded cDNAs coding for mouse heavy chain and light chain were synthesized from 1 µg of the total RNA by using MuLV Reverse Transcriptase using oligo(dT) 16 as primer. The reaction mixture was incubated at 42° C. for 15 minutes, at 99° C. for 5 minutes, and then at 5° C. for 5 minutes.

The single stranded cDNAs of $V_H$ and $V_\kappa$ were amplified by AmpliTaq® DNA Polymerase using "The mouse-specific Ig Primer Sets" (Novagen, Madison, Wis., cat. no. 69831-1) as amplification primers. The reaction mixture was heated at an initial temperature of 95° C. for 1 minute 45 seconds, then cycled 35 times at 95° C. for 15 seconds followed by 60° C. for 30 seconds. The reaction mixture was then held at 72° C. for 10 minutes. The amplified DNAs were gel-purified and cloned into the vector pGm® T Easy (Promega, cat. no. A1360). The $V_H$ and $V_\kappa$ clones obtained were screened for inserts of the expected size by PCR.

The DNA sequences of $V_H$ and $V_\kappa$ clones with DNA inserts of the expected sizes were determined by the dideoxy chain termination method. The location of the complementarity determining regions (CDRs) was determined with reference to other antibody sequences [32]. The B4 $V_H$ can be assigned to mouse heavy chains subgroup V(B), and, the B4 $V_\kappa$ was assigned to mouse kappa chains subgroup III [32]. The DNA and amino acid sequences and the CDRs of $V_H$ and $V_\kappa$ are shown in FIGS. 1 and 2, respectively.

EXAMPLE 2

Construction of Chimeric B4 Antibody Genes and their Expression by NSO Cells

1. Construction of Chimeric Antibody Genes

The chimeric B4 antibody consists of mouse-human antibody chains made by taking the variable region genes for murine mAb B4 and joining them to the human immunoglobulin constant region genes, in a manner similar to that described by Morrison et al. [19]. In this fashion, the fully murine variable regions were linked to human constant regions. The chimeric antibody provides a useful undeimmunized control with the same human constant regions, for comparisons when testing the B4-derived antibodies having deimmunized variable regions.

For the construction of the chimeric B4, the vectors VH-PCR1 and VK-PCR1 [20] were used as templates to introduce the 5' flanking sequence including the leader signal peptide, leader intron and the murine immunoglobulin promoter, and the 3' flanking sequence including the splice site and intron sequences, around the murine $V_H$ and $V_\kappa$ genes. The murine HV and VJ expression cassettes produced were cloned into pUC19 and the entire DNA sequence was confirmed.

The murine $V_H$ and $V_L$ expression cassettes were excised form pUC19 as HindIII to BamHI fragments. These were transferred to the expression vectors pSVgpt and pSVhyg [20] (FIGS. 3 and 4), which include human IgG$_1$ [48] or κ constant regions [49], respectively, and markers for selection in mammalian cells. The DNA fragments were confirmed to be correct for the expected $V_H$ and $V_\kappa$ in the pSV expression vectors by sequencing.

2. Host Cell Line for Expression of B4 Chimeric Antibody

The host cell line for antibody expression was NSO, a non-immunoglobulin producing mouse myeloma, obtained from the European Collection of Animal Cell Cultures, Porton UK(ECACC No. 85110505). The chimeric heavy and light chain expression vectors were cotransfected into NSO cells by electroporation. Colonies expressing the gpt gene were selected in Dulbecco's Modified Eagle's Medium (DMEM) supplemented with 10% fetal calf serum, 0.8 µg/ml mycophenolic acid and 250 µg/ml xanthine.

3. Detection of Antibody Expression by Human IgG ELISA

Production of human IgG was measured by ELISA. The method is as follows: ELISA plate microtiter wells were coated with sheep anti-human κ antibody in carbonate/bicarbonate coating buffer pH 9.6 (Sigma, cat. no. C3041) at 37° C. for 1 hour. Then the plate was washed three times with PBST (0.05% Tween® 20 in PBS). This procedure formed the solid-phase immunosorbent for capture of κ chain from the medium.

The conditioned media from transfected cell clone cultures were incubated in the coated wells at 37° C. for 1 hour and drained, followed by three washes with PBST. Peroxidase-conjugated sheep anti-human IgG γ chain specific antibody (The Binding Site, cat. no. AP004) was the secondary antibody and o-phenylenediamine substrate (OPD) (Sigma, cat. no. P7288) was the colorimetric reporter. Cell lines secreting human antibody were selected and expanded.

4. Production of Chimeric Antibody

The NSO transfectants secreting the highest levels of chimeric antibody were selected and expanded. Antibody was purified from 500 ml to 1000 ml static cultures by ProSep A affinity chromatography (Millipore Cat. No. 113112722). Antibody was eluted with 0.1 M glycine pH 3.0, neutralized and dialyzed into PBS. Purified antibody preparation was sterilized by filtration and stored at 4° C. The concentration of antibody was determined by IgG ELISA with comparisons to 0.1, 1, 5, 10 ng human IgG$_1$ reference standards (The Binding Site, cat. no. BP078).

5. Relative Binding Affinity of Chimeric Antibody to rsCD4 Compared to the Binding Affinity of Murine Antibody The relative binding affinity of chimeric antibody to recombinant soluble CD4 (rsCD4) was determined by ELISA.

ELISA plates were directly coated with rsCD4 (American Biotechnologies, Columbia Md.) at 0.25 µg/ml in 0.1 M carbonate buffer pH 9.5 and blocked with 3% BSA, 0.05W. Tween® 20 in PBS. Various dilutions of the chimeric antibody and the mouse antibody as the positive control were applied. Detection was with peroxidase conjugated goat anti-human IgG and sheep anti-mouse for chimeric and mouse antibodies respectively. Color was developed with OPD.

Both the chimeric and mouse antibodies provided increases in $A_{492}$ at all concentrations of antibodies when added to the solid-phase rsCD4. This assay confirmed that the cloned and sequenced heavy and light chain variable regions retained the correct recognition site. The chimeric antibody showed a 10-fold reduction in $A_{492}$ compared to that of the original mouse antibody.

EXAMPLE 3

Design and Construction of Deimmunized Variable Region Sequences

6. Design of Deimmunized V Sequences

The amino acid sequences of mouse B4 $V_H$ and $V_\kappa$ were compared to the sequences of the directory of human germline $V_H$ [33] and $V_\kappa$ [34] sequences and also to human germline J region sequences [49]. The human germline VH, J region and $V_\kappa$ sequences with the highest homologies to the murine B4 $V_H$ and $V_\kappa$ were chosen to be the reference human framework sequences.

Following identification of the reference human framework sequences, certain non-identical amino acid residues within the B4 $V_H$ and $V_\kappa$ frameworks which are surface exposed were changed to the corresponding amino acid in the human reference sequence [24]. Residues which were considered to be critical for antibody structure and binding were excluded from this process and were not altered. For example, the murine residues at the N-terminus, which are close to the CDRs in the final antibody, were retained. This process produces a sequence that is broadly similar to a "veneered" antibody as the surface residues are mainly human and the buried residues are as in the original murine sequence.

These sequences were then subjected to the in silico process of peptide threading to identify potential T cell epitopes [25], through analysis of binding to 18 different human MHC class II allotypes. Primary deimmunized $V_H$ and $V_\kappa$ amino acid and cDNA sequences were defined (B4DIVHv.1, FIGS. 5 and 7; B4DIVkv.1, FIGS. 6 and 8). As generation of the primary deimmunized sequences required a small number of amino acid substitutions which may affect the binding of the final deimmunized molecule, three other variant $V_H$s (B4DIVHv.2, B4DIVHv3., B4DIVHv4., FIGS. 5 and 7) and 2 other $V_\kappa$s (B4DIVkv.2, B4DIVkv.3, FIGS. 6 and 8) were designed.

7. Construction of Deimmunized Antibody Sequences

The deimmunized variable regions were constructed in accordance with the above designs by the method of site directed mutagenesis PCR (QuikChange™ Site-Directed Mutagenesis Kit, Stratagene, cat. no. 200518).

The cloned murine $V_H$ and $V_\kappa$ genes were used as templates for mutagenesis of the framework regions to the required deimmunized sequences. Sets of mutagenic primer pairs were synthesized encompassing the regions to be altered. The deimmunized V regions produced were cloned into pUC19 and the entire DNA sequence was confirmed to be correct for each deimmunized $V_H$ and $V_\kappa$.

Figure 3:
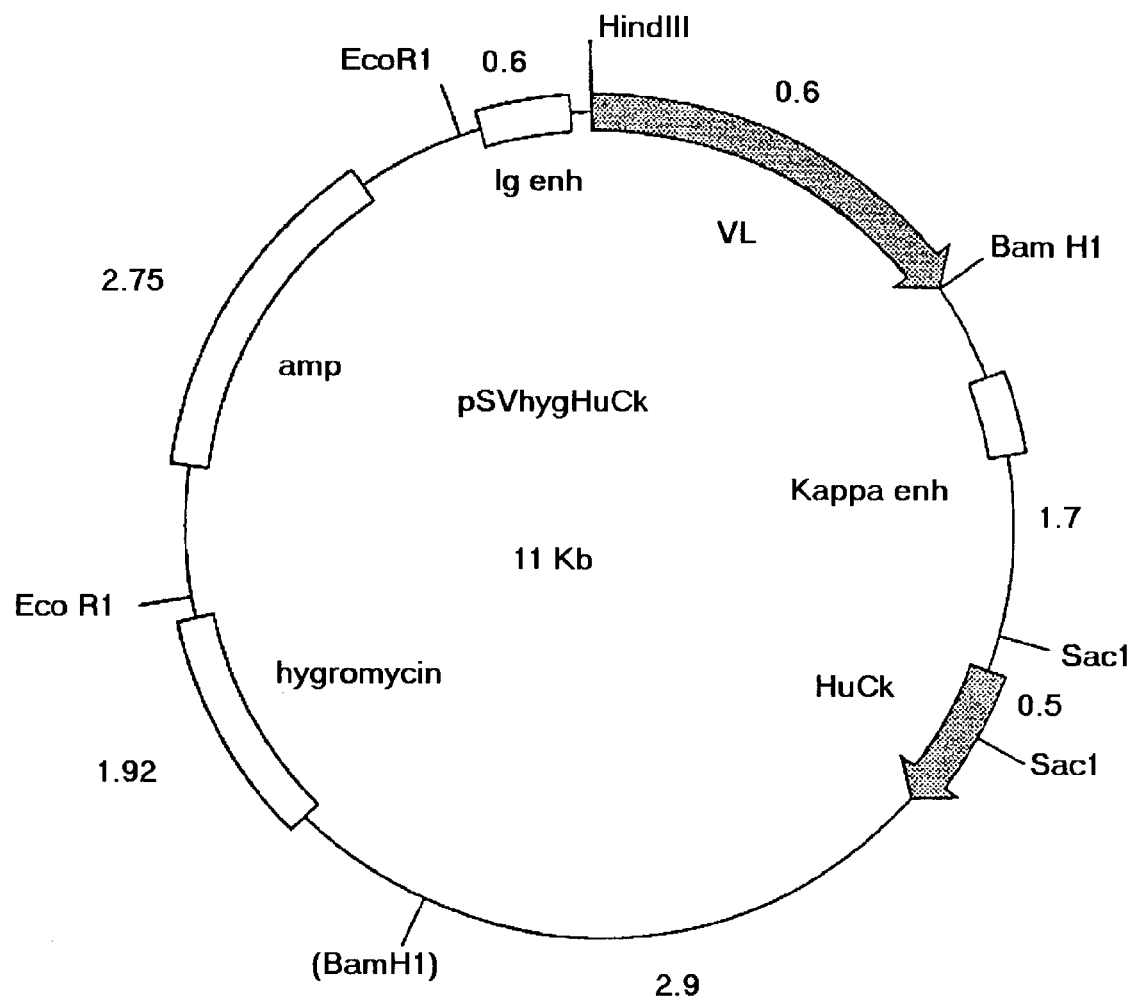
FIG. 3. Heavy chain expression vector pSVgptHuIgG1 with HV inserted, for expression of chimeric IgG1 heavy chain, mAb B4 mouse VH fused to human CH1, in NSO cells. Ig enh is heavy chain enhancer.
Figure 4:
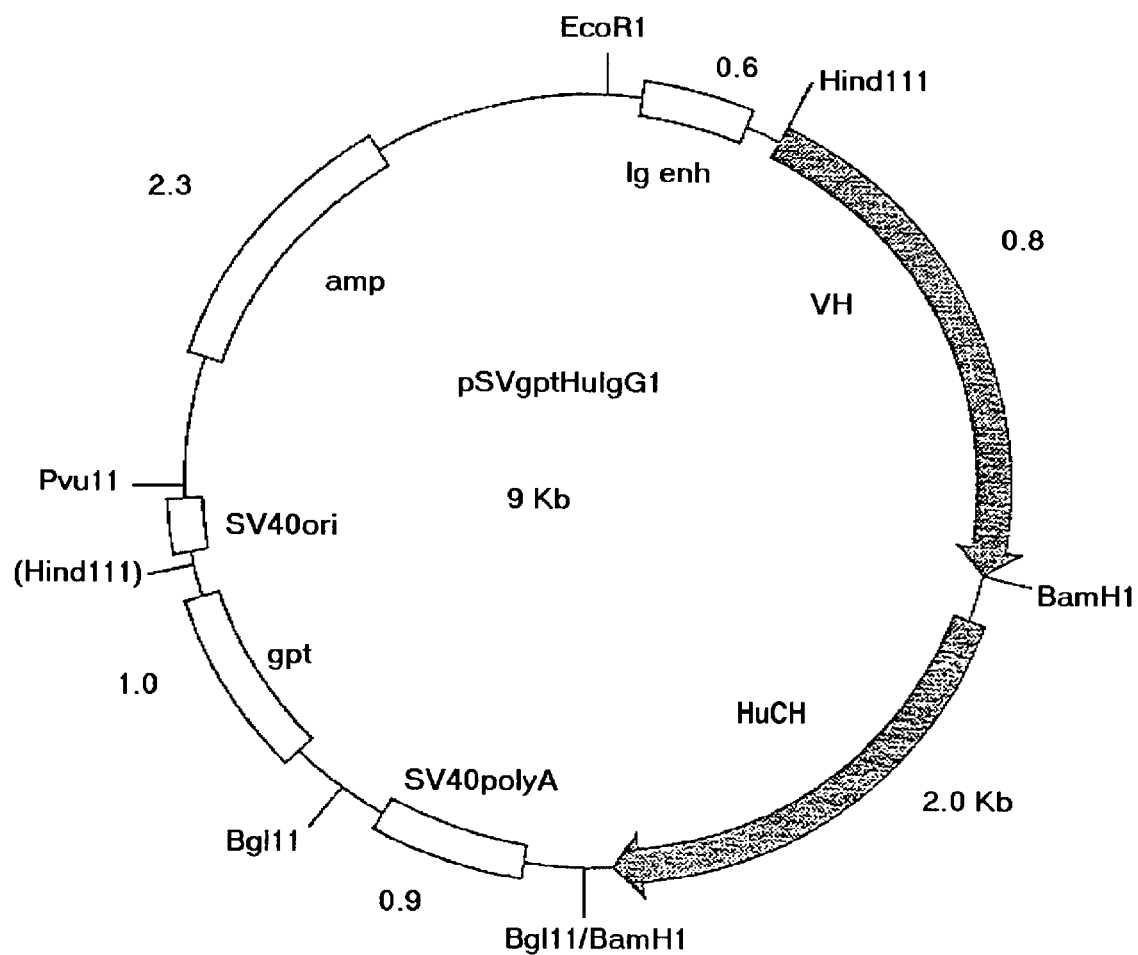
FIG. 4. Light chain expression vector pSVhygHuK with $V_κ$ inserted, for expression of chimeric IgG light chain, mAb B4 mouse $V_κ$ fused to human $C_κ$, in NSO cells. Ig enh and Kappa enh are heavy and κ chain enhancers.

The deimmunized heavy and light chain V-region genes were excised from pUC19 as HindIII to BamHI fragments, and were transferred to the expression vectors psvSVgpt and pSVhyg (FIGS. 3 and 4). The DNA sequences were confirmed to be correct for the deimmunized $V_H$ and $V_\kappa$ in the expression vectors.

EXAMPLE 4

Characterization of Deimmunized Antibody Expressed by NSO Cells

8. Expression of Deimmunized Antibodies

The host cell line for antibody expression was NSO, a non-immunoglobulin producing mouse myeloma, obtained from the European Collection of Animal Cell Cultures, Porton UK(ECACC No. 85110505).

The deimmunized heavy and light chain expression vectors were cotransfected in a variety of combinations (12 combinations) into NSO cells by electroporation. Colonies expressing the gpt gene were selected in Dulbecco's Modified Eagle's Medium (DMEM) supplemented with 10% fetal calf serum, 0.8 µg/ml mycophenolic acid and 250 µg/ml xanthine.

Production of human IgG by transfected cell clones was measured by ELISA for human IgG. Cell lines secreting antibody were selected and expanded.

9. Production of Deimmunized B4 Antibodies

NSO transfectants secreting the highest levels of chimeric antibody were selected and expanded. Antibody was purified from 500 ml to 1000 ml static cultures by ProSep A affinity chromatography (Millipore, Cat. No. 113112722). Antibody was eluted with 0.1 M glycine pH 3.0, neutralized and dialyzed into PBS. Purified antibody preparation was sterilized by filtration and stored at 4° C. The concentration of antibody was determined by ELISA.

10. The rsCD4 Binding Affinity of B4 Deimmunized Antibodies

Figure 9:
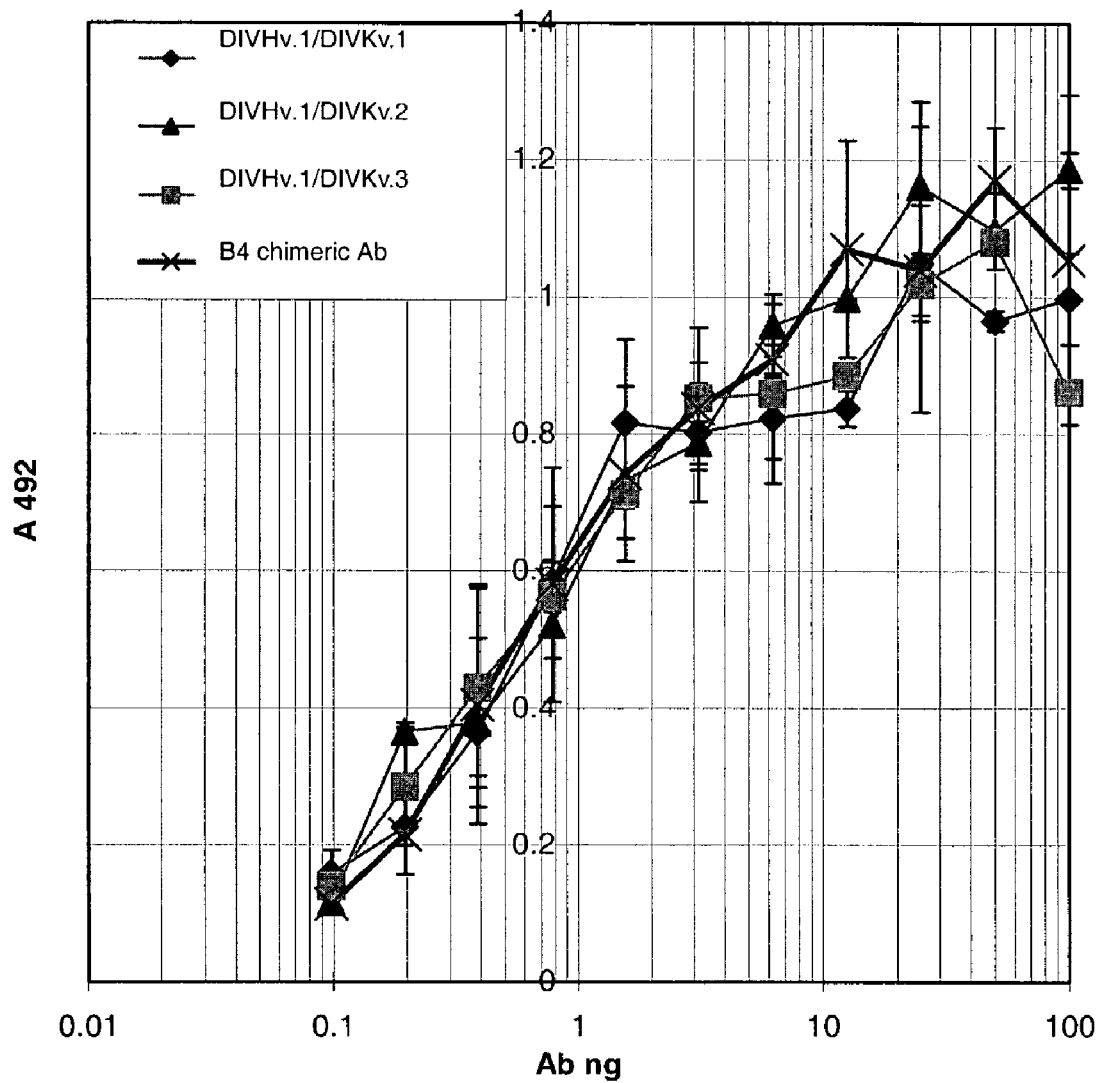
FIG. 9. Relative affinities for the binding of rsCD4 by the B4 chimeric antibody and DIVH1/VK1-3 deimmunized antibodies.
Figure 10:
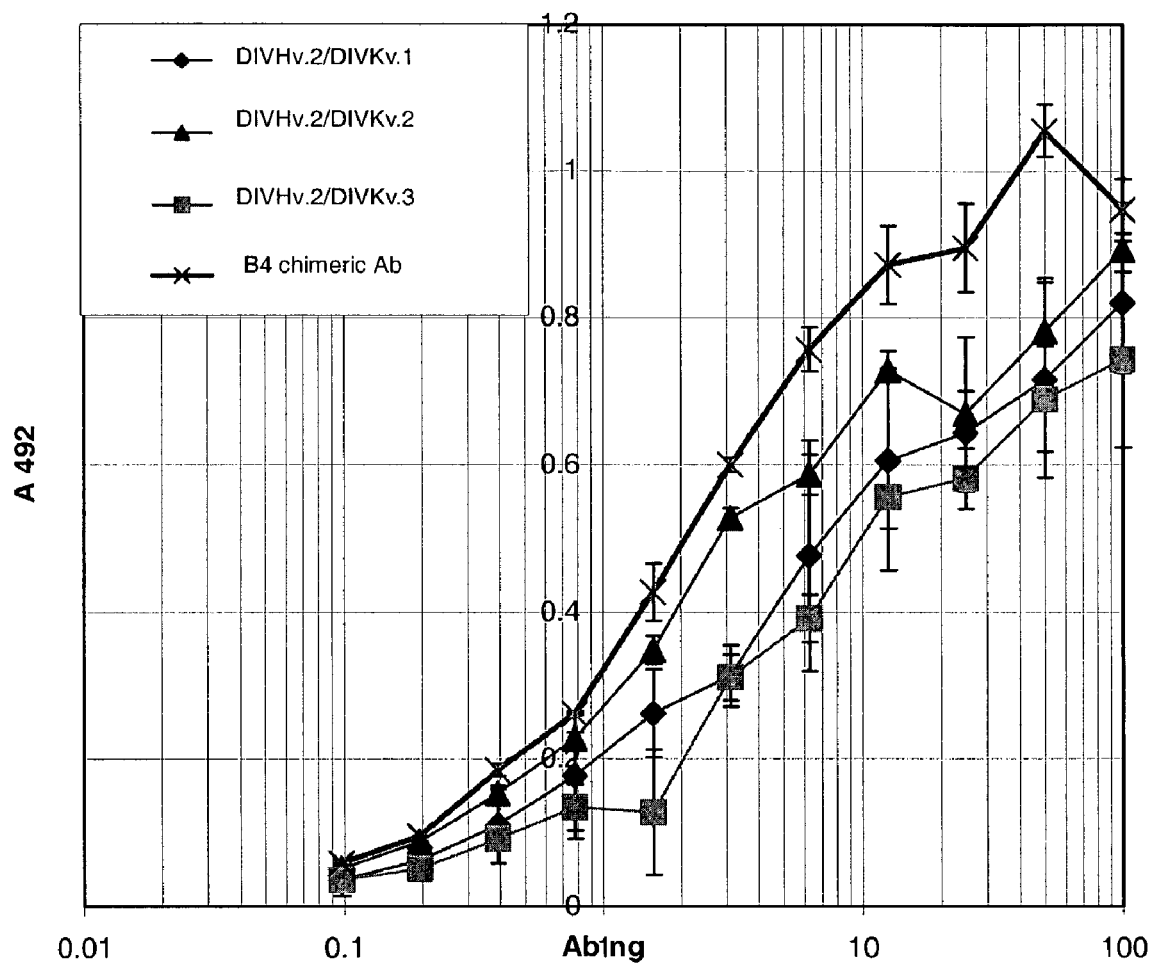
FIG. 10. Relative affinities for the binding of rsCD4 by the B4 chimeric antibody and DIVH2/VK1-3 deimmunized antibodies.
Figure 11:
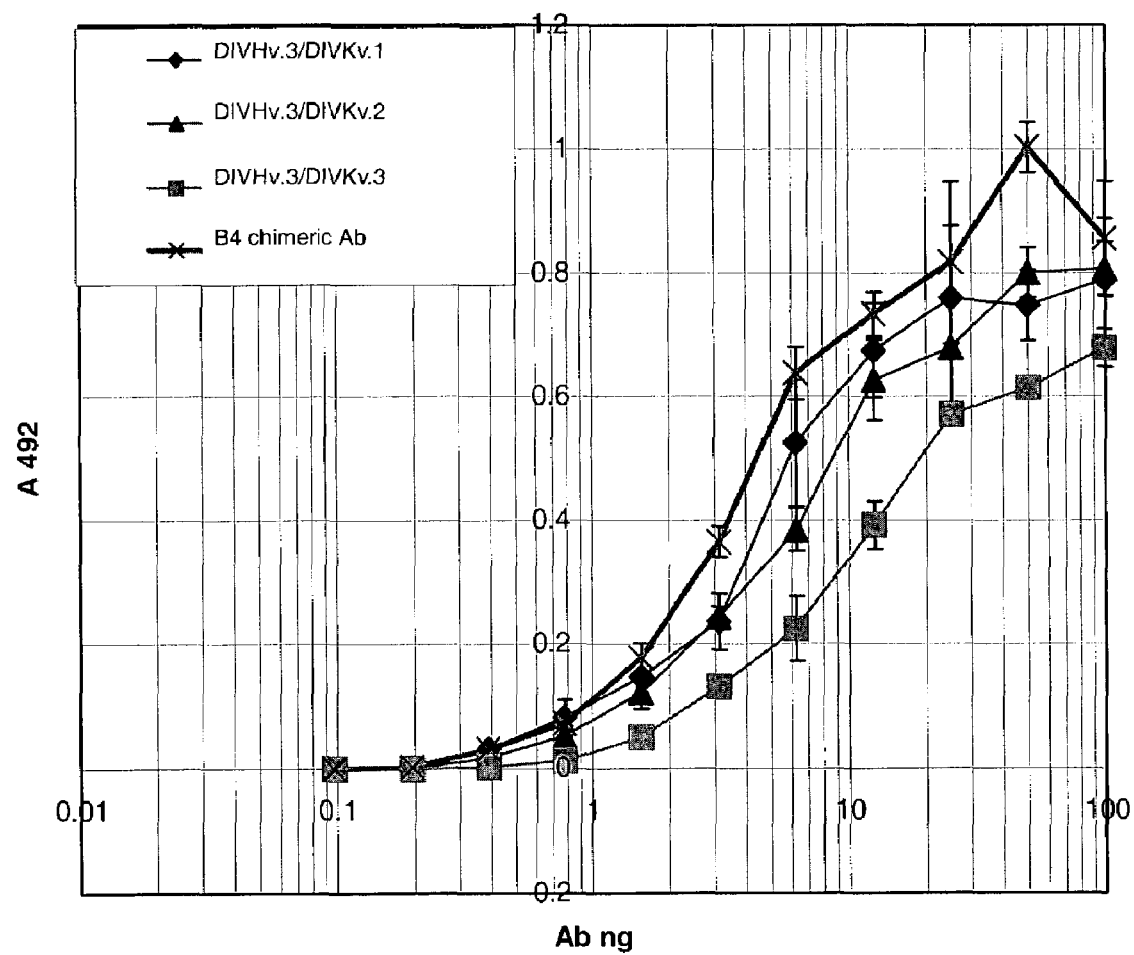
FIG. 11. Relative affinities for the binding of rsCD4 by the B4 chimeric antibody and DIVH3/VK1-3 deimmunized antibodies.
Figure 12:
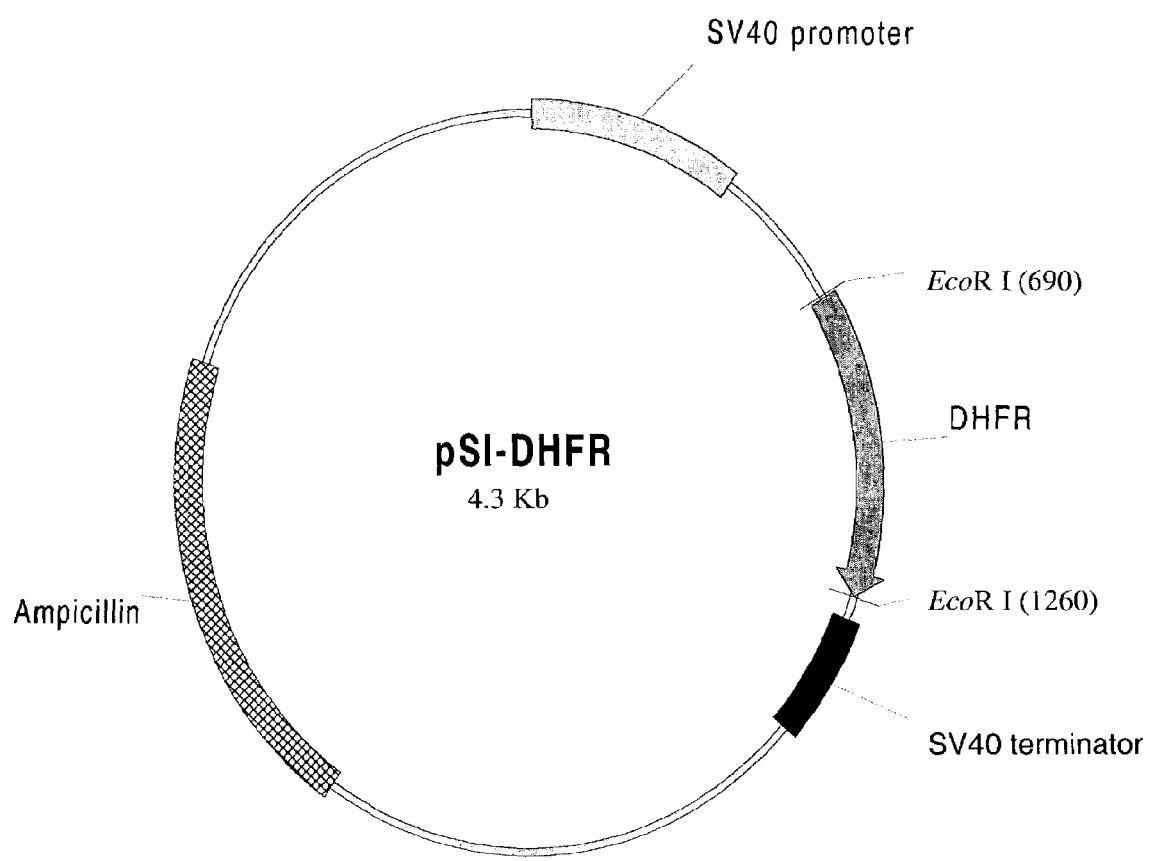
FIG. 12. The dhfr gene expression vector, pSI-DHFR.

The results of the binding assay for four deimmunized B4 heavy chains combined with three deimmunized light chains are shown in FIGS. 9-11.

The antibodies composed of deimmunized heavy chain version 1 combined with deimmunized light chain versions 1, 2, or 3 showed equivalent binding to rsCD4 compared to the chimeric antibody. Binding by antibodies composed of deimmunized heavy chains versions 2, 3, or 4 combined with deimmunized light chains versions 1 or 2 was less than three-fold reduced compared to the chimeric antibody. The antibodies composed of deimmunized heavy chain versions 2, 3, or 4 combined with deimmunized light chain version 3 showed five-fold reductions in binding to rsCD4.

11. Virus Neutralization Assay

Virus stocks. Subtype A patient isolate UG/92/029, was acquired from the WHO Network for HIV Isolation and Characterization. Subtype C patient isolate ZIM748 was a gift from D. Katzenstein, Stanford University. Subtype D patient isolate UG266, subtype E SI patient isolate TH32036, were supplied by the U.S. Military HIV Research Program (Silver Spring, Md.). Subtype E patient isolate TH 32036 was also received as a gift from J. Bradac, NIAID (NIH, Bethesda, Md). Patient isolates were passaged in PBMC. T cell line-adapted HIV-1 isolate MN was grown in H9 cells, except for a sample of MN passaged in PBMC.

Figure 13:
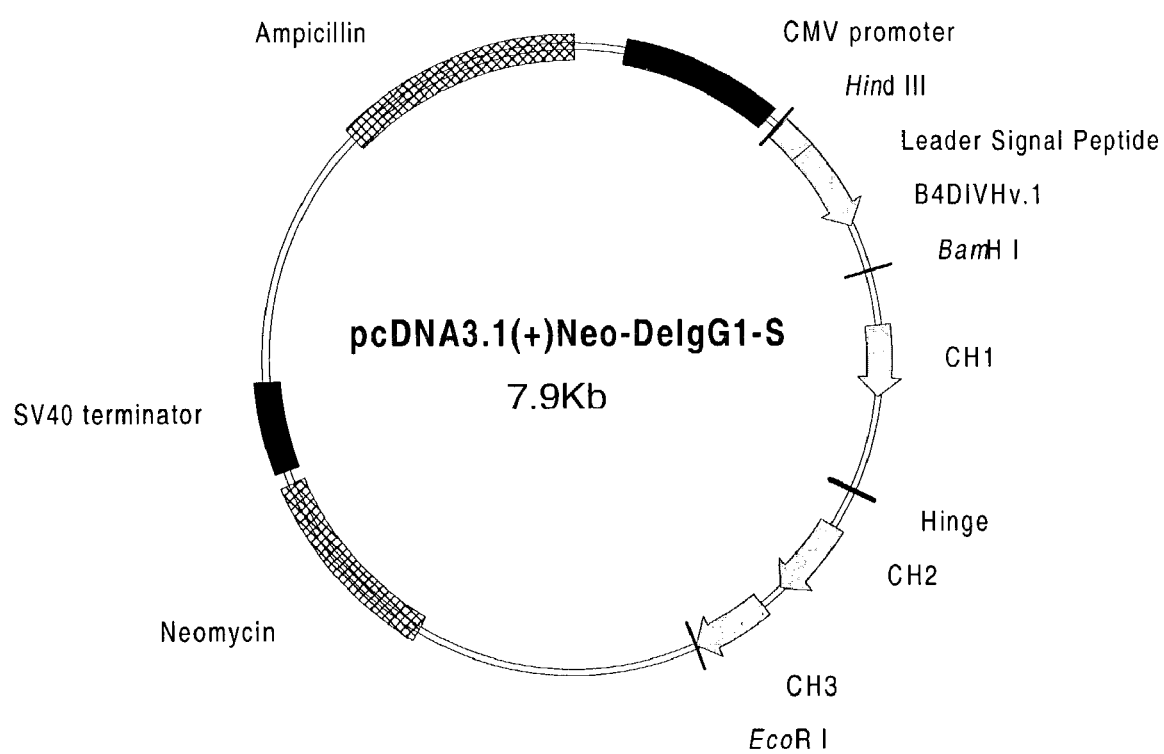
FIG. 13. Deimmunized heavy chain expression vector, pcDNA3.1(+)Neo-DeIg1-S, with B4DIVHv.1, joined to human $C_H$, for expression in CHodhfr− cells.

Virus neutralization activity assay of B4 deimmunized IgG produced in NSO cells. The MT-2 microplaque assay was carried out as described [36] except that heat-inactivated sera were serially diluted in 50% high glucose DMEM with 15% FBS, antibiotics, 2% glutamine and bicarbonate buffer, and 50% pooled, defibrinated normal human plasma. Neutralization assays on mitogen-stimulated PBMC were done with HIV essentially as described [50].

The neutralizing activity of deimmunized B4 $IgG_1$ produced by NSO cells was defined as the antibody concentration that provided a 50% reduction in plaques as compared with controls containing no antibody. Antibody concentrations for the 50% endpoint were derived by interpolation between antibody dilutions. The comparisons of the four heavy chain variants (VHv.1-4), all combined with deimmunized κ chain version 1 (VKv.1), showed that the antibody having the version 1 heavy chain had high neutralizing activity against all of the HIV-1 primary isolates, with activities approaching that of murine mAb B4 for HIV-$1_{VL135}$, HIV-$1_{UG029}$ and HIV-$1_{TH036}$ (Table 1).

The deimmunized B4 antibodies were ineffective against the T cell line-adapted HIV-$1_{MN}$ virus. Deimmunized antibodies comprising with κ chain versions 2 or 3 either were comparable or had lower neutralizing activities (Table 2). The comparisons of the 12 variants showed that the antibody having the DIVHv.1 heavy chain and DIVKv.1 had high neutralizing activity against all of the HIV-1 primary isolates, with activities approaching that of the murine mAb B4.

EXAMPLE 5

Establishment of Stable and Highly Expressing Deimmunized B4 Antibody CHO Clone

B4DIVHv.1 and B4DIVKv.1 were chosen respectively as the heavy and light chains to be expressed in CHO cells.

12. Cell Line

The host cell line for production level antibody expression was Chinese hamster ovary cells lacking the enzyme dihydrofolate reductase ($CHOdfhr^-$), obtained from the Culture Collection and Research Center (CCRC, 60133) of Food Industry Research and Development Institute, Taiwan.

The cells were maintained in Isocoves Modified Dulbecco's Medium (IMDM, Sigma cat. no. I-3390) supplemented with 10% dialyzed fetal calf serum (DFCS, Gibco cat no. 26400-044)) plus hypoxanthine and thymidine (Gibco, cat no. 11067-030). The DHFR marker is used for amplification and selection. Expression by the dhfr gene could be amplified by challenging with the dihydrofolate reductase inhibitor, methorexate (MTX).

When the dfhr genes are amplified, other neighboring genes often are co-amplified, so that after each round of amplification cells were subcloned to select for clones with increased production rates.

13. Plasmid Construction

Plasmid expressing DHFR gene. The cDNA for the dhfr gene was synthesized by the GeneAmp® RNA PCR Kit (Perkin Elmer part no. N808-0017) from total RNA of NSO cells. The cDNA for the dhfr gene was inserted into the mammalian expression vector, pSI (Promega, cat. no. E172A), at the EcoR1 site, downstream of the SV40 enhancer and early promoter and upstream of the SV40 terminator, for high level constitutive expression (FIG. 12).

Plasmid expressing B4DIVHv.1 heavy chain. The DNA fragment coding the chimeric B4 heavy chain was obtained by PCR amplification from pSVgpt B4 chimeric IgG (FIG. 3) as template. The chimeric IgG gene was inserted at the HindIII and EcoRI sites of the mammalian expression vector pcDNA3.1Neo (Invitrogen, Carlsbad, Calif., cat. no. V790-20). The insertion site is downstream of the CMV enhancer and early promoter for high level expression, and in front of polyadenylation signal and transcription termination sequences from bovine growth hormone (BGH) for enhanced mRNA stability. Then, the variable region was replaced with the variable region of B4DIVHv.1 through the use of the HindIII and BamHI to obtain the plasmid expressing B4DIVHv.1 heavy chain (pCDNA3.1(+)NeoDeIgG1-S, FIG. 13).

Plasmid expressing aglycosylated B4DIVHv.1 heavy chain. Removing the N-glycosylation site in the Fc region of $IgG_1$ by mutation has been shown to abolish the ability of $IgG_1$ to bind to human Fc R1, to activate complement, and to bind C1q [43]. Therefore, an aglycosylated deimmunized mAb B4 has the potential to be less depleting of CD4+ cells and less immunotoxic than a glycosylated antibody.

To remove the site for N-linked carbohydrate, the AAC codon for $Asn_{297}$ of the DIVHv.1 heavy chain was mutated to CAC for His by site-direct mutagenesis PCR (Invitrogen).

Figure 14:
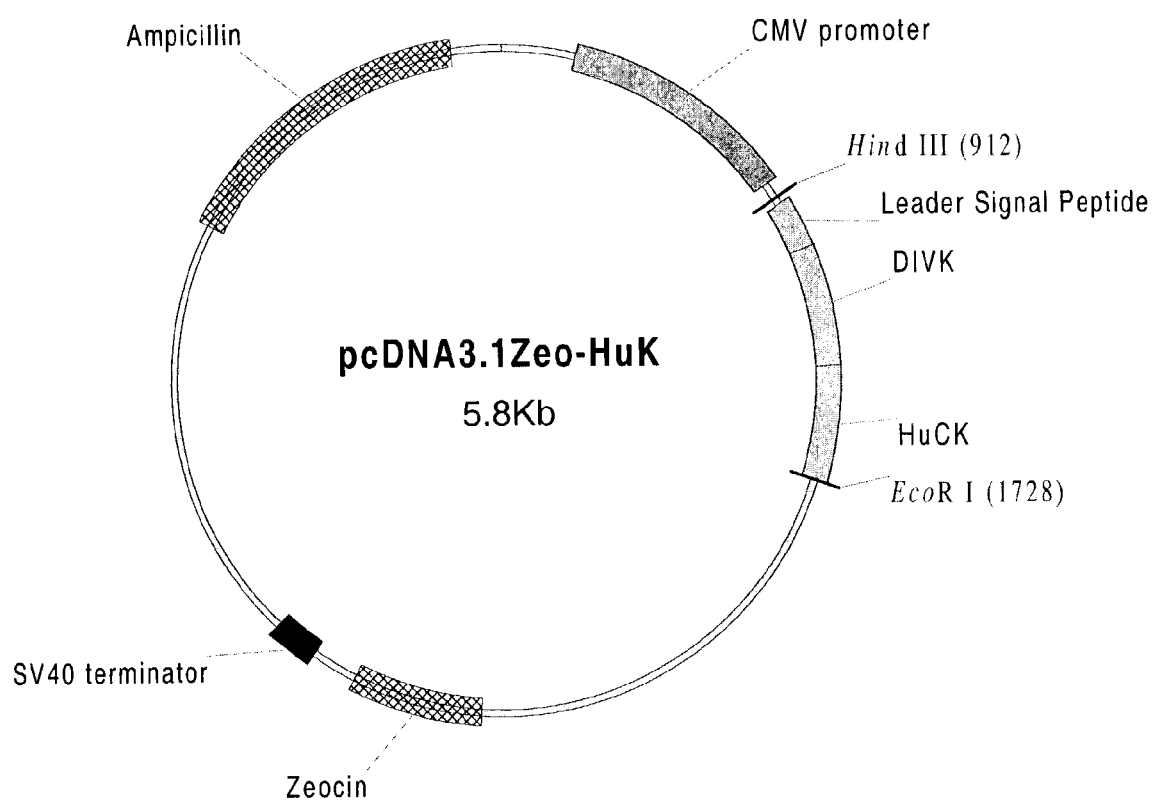
FIG. 14. Deimmunized K chain expression vector, pcDNA3.1Zeo-HuK, with B4DIVKv.1, joined to human $C_κ$, for expression in CHodhfr− cells.

Plasmid expressing B4DIVkv.1 light chain. B4DIV.1 full light chain was assembled from DIV v.1 variable and human κ chain constant regions by PCR amplifications. The DIVKv.1 region was copied from pUC19-B4DIVKv.1 as template. Human κ constant region was copied from the B4 chimeric κ chain ($V_\kappa$) of pSVhygHuCK as template. The complete B4DIV.1 light chain DNA fragment was inserted into pCDNA3.1zeo (Invitrogen, cat. no. V860-20) at the HindIII and EcoR1 sites. The insertion site is downstream of the CMV enhancer and early promoter for high level expression, and upstream of polyadenylation signal and transcription termination sequences from BGH for enhanced mRNA stability (FIG. 14).

Figure 15:
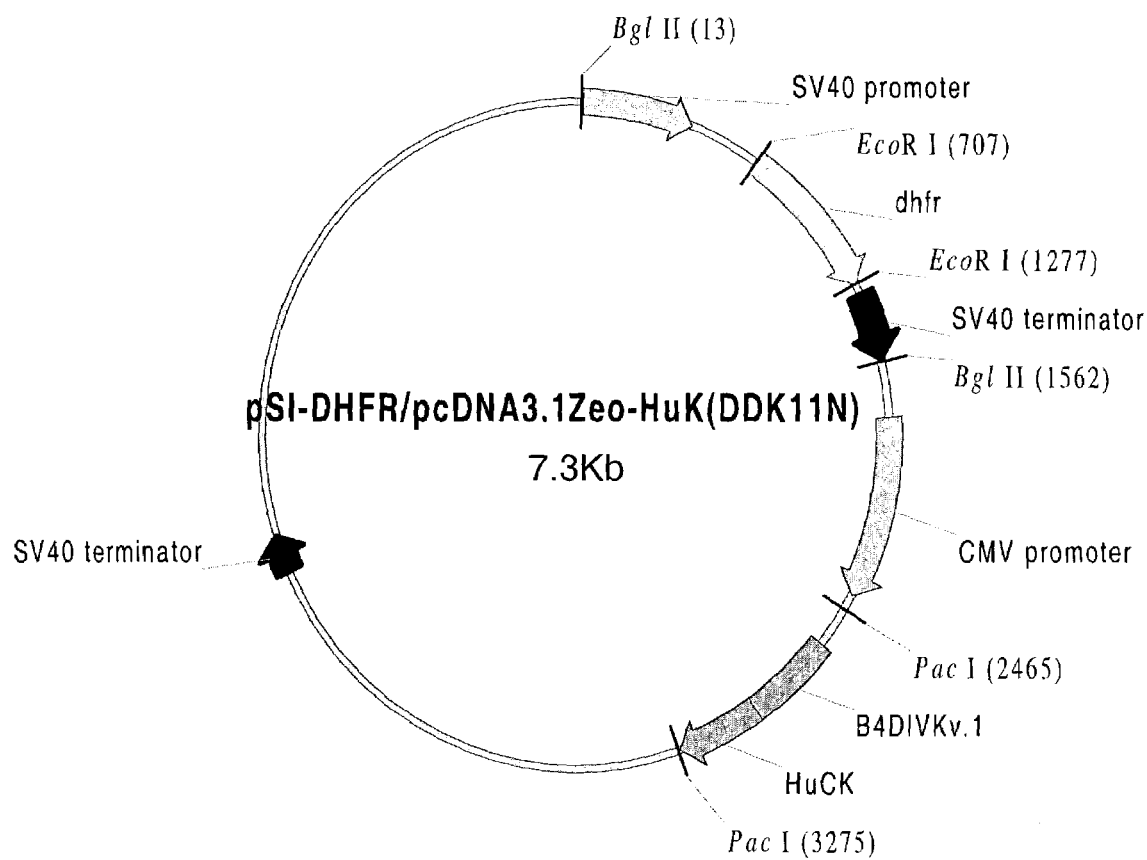
FIG. 15. Deimmunized κ chain and DHFR expression vector, pSI-DHFR/pcDNA3.1zeo-HuK(DD11N), with B4DIVKv.1 joined to human $C_κ$, for co-expression with dhfr in CHodhfr− cells.

Plasmid co-expressing DHFR and B4DIVkv.1 light chain. A plasmid containing both DHFR and B4DIVkv.1 light chain expression units was constructed by insertion of dhfr gene expression unit in front of κ chain expression unit. The dhfr gene expression unit was obtained from the PCR product by using pSI-DHFR as template and cloned into the pcDNA3.1zeoB4DIVkv.1 plasmid at the BglII site (FIG. 15).

14. Expression of B4 DIVHv.1-DIVKv.1 Antibody in CHOdhfr− Cells pcDNA3.1zeoB4DIVHv.1 and pcDNA3.1zeoB4DIVkv.1/DHFR were co-transfected into CHOdhfr− cells by electroporation. Colonies were selected by culturing in IMDM medium containing with 10% DFCS, geneticin (Gibco, cat. no. 10131-027) and 0.005 µM MTX (Sigma, St. Louis, Mo., cat no. M8047) but without HT supplement. The cells expressing DHFR and heavy chain were grown in this selection medium. Production of human IgG was measured by ELISA. Cell lines secreting antibody were selected and expanded.

15. Establishment of High-Level Deimmunized B4 Producer Clones by MTX-mediated DFHR Gene Amplification The expression of DFHR and IgG was amplified for greater production of deimmunized mAb B4 by stepwise increases in MTX concentrations [42]. Clones were exposed to incrementally increasing MTX concentrations from 0.005 to 5 µM. The duration of each concentration treatment was 3-4 weeks. Between each cycle of amplification, cells were subcloned and selected for increased levels of IgG productivity.

16. Establishment of Stable High Producer Deimmunized B4 Cell Lines by Single Cell Cloning Clonal lines from the best producing amplified subclones were established using limiting dilution. Subclones were resuspended in selective medium at concentrations of 0.1, 0.5 and 0.25 cells/200 µl and plated into 96 well dishes. Cells were cultured in selective medium for 3-4 weeks before screening. Following incubation, 10 µl of culture medium was removed from each culture for determination of human IgG expression by ELISA. The high producer clones were selected and expanded and cryogenic cell line stocks were made. The IgG productivity of the best producers from these amplification steps was about 10-20 pg/cell/day. Productivity had been amplified about 100-200-fold, from initial expression levels of about 0.1 pg/cell/day.

17. Production of N-glycosylated and N-aglycosylated Antibodies in CHO Cells

CHO transfectants with the wild type heavy chain and with the $Asn_{297}$ of H chain mutated to His were expanded. Antibody was purified from 500 ml to 1000 ml static cultures by ProSep A affinity chromatography (Millipore cat. no. 113112722). Antibody was eluted with 0.1 M glycine pH 3.0, neutralized and dialyzed into PBS. Purified antibody preparation was sterilized by filtration and stored at 4° C. The concentration of antibody was determined by ELISA.

18. Identification of N-aclycosylation by SDS-PAGE

The antibodies purified from the clone with $Asn_{297}$ heavy chain and from the transfectants with $Asn_{297}$ mutated to His with/without N-glycodiase F treatment were analyzed by 10% SDS-PAGE and stained by Coomassie Blue and glycoprotein stains (GelCode Glycoprotein Stain, cat. no. 24562, Pierce, Rockford Ill.

The antibodies purified from the clone mutated at $Asn_{297}$ to $His_{297}$ displayed faster gel mobility and less intense glycoprotein staining than the glycosylated deimmunized antibody. The N-glycosidase F treatment did not change the gel-mobility and glycoprotein staining intensity of the mutant antibody but increased the gel-mobility and decreased the glycoprotein staining intensity of wild N-glycosylated antibodies. After N-glycosidase F treatment, wild type and mutated antibodies had the same gel-mobilities (FIG. 16A) and glycoprotein staining intensities (FIG. 16B), confirming the already aglycosylated status of the mutated antibody.

19. Virus Neutralization Activity Assay of B4 Deimmunized IgG Produced by CHO Cells The MT-2 microplaque assay was carried out as described above. The neutralizing activity of deimmunized B4 $IgG_1$ produced by CHO cells was defined as the antibody concentration that provided the 50% endpoint reduction in plaques as compared with controls containing no antibody (Table 3). Antibody concentrations for the 50% endpoints were derived by interpolation between antibody dilutions.

EXAMPLE 6

Adaptation of B4 Deimmunized CHO Clones to Serum-free Suspension Culture

20. Suspension Culture Adaptation

A 75T flask having confluent deimmunized B4 CHO culture was trypsinized and resuspended into a spinner flask (Bellco, Vineland, N.J.) containing 50 ml Isocoves Modified Dulbeccos' Medium (IMDM, Sigma cat. no. I-3390) supplemented with 10% dialyzed fetal calf serum (DFCS, Gibco cat. no. 26400-044). Spinner flask suspension cultures were magnetically agitated and maintained in a $CO_2$ incubator under the same conditions of temperature and humidity as monolayer cultures.

Every 2-3 days, the viable cell density of the culture was determined and adjusted to $1\text{-}3\times10^5$ cell/ml medium by dilution with fresh medium. The growth rate and cell viability of the culture were monitored closely during the first few weeks of culture.

21. Adaptation to Serum-free Medium

Once the growth performance of the suspension culture was stabilized, the culture was centrifuged and the cells were resuspended into serum free medium (SFMII, Gibco BRL, Rockville, Md., cat. no. 31033-020). Every 2-3 days, the viable cell density of the culture was determined and adjusted to $1-3\times10^5$ cell/ml medium by dilution with fresh medium. The growth rate and cell viability of the culture were monitored closely during the first few weeks of culture.

22. Production of Deimmunized B4 Antibodies in Serum-Free Suspension Culture

The deimmunized B4 clones, adapted to suspension culture in serum-free medium, were initially cultured at a cell density of $2\times10^5$ in a 100 ml spinner flask (Bellco) in Gibco SFMII medium. Cultures were serially scaled up by transfer to 250 ml and 500 ml spinner flasks, when the cell densities reached $6\times10^5$cell/ml. Antibody was purified from 500 ml serum-free suspension cultures by ProSep A affinity chromatography (Millipore cat. no. 113112722). Antibody was eluted with 0.1 M glycine pH 3.0, neutralized and dialyzed into PBS. Purified antibody preparation was sterilized by filtration and stored at 4° C. The concentration of antibody was determined by ELISA.

EXAMPLE 7

Complement Fixation Analysis of the Deimmunized B4 Antibodies Expressed by rCHO Clones A complement consumption assay was used to assess the complement fixation property of murine B4 as compared to its deimmunized counterparts. The assay entailed binding each of the B4 monoclonal antibodies to the CD4 complex site on the surface of freshly prepared human CD4$^+$ cells. This was followed by allowing the antibody to partially fix a given amount of rabbit complement. Complement remaining in the reaction was assayed against sensitized sheep red blood cells.

Human CD4$^+$ cells used in the assay were fractionated from heparinized peripheral blood collected by venous puncture of a normal blood donor. The whole blood was diluted 1:1 (v/v) with serum-free RPMI-1640 (Gibco, cat no. 21870-076). 10.0 ml of diluted blood was then layered onto 9.0 ml of Ficoll Hague™ Plus (Amersham Biosciences, cat no. 17-1440-02) in a 50.0 ml centrifuge tube (Nunc cat no. 373660).

Fractionation of lymphocytes was achieved by centrifugation of the blood at 2000 rpm for 30 minutes at room temperature. The buffy coat containing the peripheral blood mononuclear cells (PBMC) at the interface of Ficoll Hague™ and the diluted serum was collected, washed three times with Veronal buffer (pH 7.6) which was made up of: 9.1 mM sodium barbital (Merck, cat no. 1.06318.0100); 15.6 mM barbital (Merck, cat no. 1.00276.0100); 0.73 M sodium chloride; 2.5 mM magnesium chloride; 2.5 mM calcium chloride. PBMC were then resuspended at $17.0\times10^7$ per ml in the same Veronal buffer.

Complement fixation assay was carried out by first adding 30.0 µg of the individual purified monoclonal antibody to 200.0 µl of PBMC preparation ($3.6\times10^6$ cells in an Eppendorf vial), and the mixture was incubated for 2 hours at room temperature to allow binding. Ninety (90.0) µl of rabbit complement (Rockland, cat no. C304-0010) pre-diluted at 1:15 in Veronal buffer was then added to the reaction mixture, and complement consumption was allowed to occur by incubating the final reaction mixture for 10 minutes at 37° C. Three hundred fifty (350) µl of sensitized sheep red blood cell (SRBC) suspension was (prepared by treating 3.0 ml of 100.0% SRBC from Rockland, cat no. R406 which had been washed twice with Veronal buffer with 100.0 µl of anti-SRBC antiserum from Rockland, cat no. 113-4139 for 30 minutes at 37° C.

The final SRBC suspension (made up in 10.0 ml of Veronal buffer) was then immediately added, and the whole reaction mixture was further incubated for 1 hour at 37° C. to assay for the residual complement present in the reaction mixture. Reaction vials were centrifuged for 1 minute at 5000 rpm in a microfuge at the end of the incubation period to spin down any remaining whole SRBC.

Lysis of SRBC was detected by aliquoting 150.0 µl of supernatant from each reaction vial into an individual well of a 96-well ELISA plate (Becton Dickinson, cat no. 353915), and reading the absorbance at 540 nm in a spectrophotometer. The results were expressed as per cent of control lysis (without monoclonal antibodies) (FIG. 17).

EXAMPLE 8

Immunogenicity Analysis of Deimmunized Antibodies

An in vitro priming culture system was employed to investigate the capability of the individual monoclonal antibodies (e.g., mAbs B4, DIVHv1/VK1 #7, or DIVHv1/VK1 #16) to stimulate human PBMC. PBMC used in this study were fractionated using the method described in Example 7 above.

In vitro PBMC cultures were prepared by plating $2.5\times10^6$cells per well in 1.5 ml of complete medium, RPMI-1640 supplemented with Penicillin and Streptomycin (Gibco, cat no. 10378-016) and fetal bovine serum (Gibco, cat no. 10099141), in 24-well tissue culture plates (Corning, cat no. 3254). Monoclonal antibodies were individually added to each PBMC culture at 10.0 µg per ml. Separate cultures were also set up by either adding Concanavalin A (Sigma, cat no. C 5275) at 2.0 µg per ml., or Pokeweed mitogen (Sigma, cat. no. L-8777) at 10.0 µg as positive controls, or without mitogen and monoclonal antibody as negative control. Duplicate cultures were set up for each stimulation condition tested. Culture supernatants were collected at days 3, 5, 7 and 9 after culture initiation, and stored at −70° C. until tested.

Cytokines in the antigen/mitogen stimulated-human PBMC culture supernatants were tested for the presence of Interleukin-2 (IL-2), Interleukin-4 (IL-4), Interleukin-10 (IL-10), Interferon-gamma (IFN-γ) and Tumor Necrosis Factor-alpha (TNF-α) using cytokine kits purchased from eBioscience (USA). The kits used were: IL-2 (cat no. 88-7026-22); IL-4 (cat no. 88-7046-22); IL-10 (cat no. 88-7106-22); IFN-γ (cat no. 88-7316-22), and TNF-α (cat no. 88-7346-22).

Assays were carried out by following the protocols given by the manufacturer. Results were obtained as shown in Table 4.

EXAMPLE 9

Clinical Evaluation of Deimmunized Antibodies

The safety, immunogenicity, pharmacokinetics and efficacy of intravenously administered deimmunized monoclonal antibody, e.g., DH1DK1NS0#16 or DH1DK1NS0#7 is studied in humans after a single-dose administration, in a dose escalation trial. The study uses two groups of HIV-infected patients (two patients per group) who have failed two courses of HAART therapy. There is no placebo group. Groups one and two are given antibody DH1DK1NS0#16 or DH1DK1NS0#7 at doses of 1 mg/kg and 5 mg/kg, respectively. The doses are given intravenously by bolus administration on day 0.

Blood and serum samples are taken on day 0 before infusion, approximately 10 minutes after infusion, and at 1 and 12 hours after infusion. Then, blood and sera are collected at 24 hours, 48 hours and days 3, 7, 14, 21, 28, 35, 42, 49, and 56.

Safety is assessed by physical examination, blood chemistry, complete cell count and recording adverse events. Immunofluorocytometric analysis for lymphocyte markers by FACS is used to assess the blood at weekly intervals for evidence of immunosupression.

Validated methods are available to monitor for the following markers: CD3/CD4, CD3/CD8, CD14/CD45, CD20/CD45, and anti-human $IgG_1$-FITC. DIH1DK1NS0#7 or DIH1DK1NS0#16 plasma levels are followed for each bleed by ELISA, using rsCD4 as the solid phase immunoadsorbant, for determination of pharmacokinetics. Immunogenicity is monitored by determining serum levels of anti-DIH1DK1NS0#7 or DIH1DK1NS0#16 by ELISA, using the antibody as solid phase immunoadsorbant.

For efficacy, HIV plasma RNA levels are determined weekly by quantitative RT-PCR assay.

EXAMPLE 10

Production of B4 Deimmunized Antibodies in Transgenic Plants

Transgenic plants may be used as an economically advantageous means to produce deimmunized antibodies. A dicotyledonous plant, tobacco (*Nicotiana tabacum*), transformed with *Agrobacterium tumefaciens* vectors bearing the cDNAs for the heavy and light chains of deimmunized aglycosylated clone no. 7, is a useful plant bioreactor for production of B4 deimmunized antibody.

The cDNA that encodes the complete heavy chain of the deimmunized B4 antibody DIH1DK1NS0#7, including the aglycosylated $IgG_1$ $C_H$, the B4DIVHv.1 $V_H$ and leader sequence, is excised from vector pcDNA3.1(+)Neo-DeIg1 (B4DIVHv.1)-S (FIG. 13) using restriction enzymes Hind III and Eco RI. The cDNA that encodes the complete deimmunized B4 chain, including the human κ $C_H$, the B4DIVKv.1 $V_κ$ and leader sequence, is excised from vector pcDNA3.1(+) Zeo-HuK(B4DIVKv.1)-S (FIG. 14) with Hind III and Eco RI. The Ig-chain encoding cDNA fragments are ligated into pMON 530, a constitutive plant expression vector that includes the cauliflower mosaic virus 35S promotor.

The recombinant vectors are transformed into *E. coli* DH5—and transformants are screened for the presence of the Ig cDNA using radiolabeled PCR products from the cloned cDNAs. Plasmids from positive transformants are introduced into *Agrobacterium tumefaciens*. Leaf discs from *N. tabacum* are infected with cultures of the recombinant *A. tumefaciens*. Shoots and rooted plantlets are regenerated from the candidate transgenic plant cells.

Leaf extracts are prepared and production by the plants of either heavy chain or kappa chain is detected by ELISA for the human heavy and light chains. Those that express heavy chains are crossed with those expressing kappa chains, by cross pollination. These procedures have been described [52].

Leaf extracts are prepared from the hybrids and transgenic plants expressing the complete deimmunized antibody DIH1DK1NS0#7 are screened by ELISA for human IgG. The plant-expressed antibodies from the reactive plants are selected for binding function and neutralization activities by comparison to the activities of the antibody of clone #7, using the rsCD4 ELISA and virus neutralization assay described in Example 4.

Alternatively, a monocotyledonous plant, maize (*Zea mays*), is used for improvements in the level of transgenic plant product expression and stability, over that of a dicotyledonous plant. It is particularly advantageous to use seed-storage promotors for tissue-specific expression in corn endosperm [53].

The promoters from zein protein genes are particularly useful for this effect. Zein proteins are storage proteins whose synthesis occurs in developing maize endosperm. The zein promotors are upregulated until the grain reaches maturity [54]. Accordingly, the cDNAs that encode the heavy and κ chains of deimmunized antibody DIH1DK1NS0#7 are respectively excised from pcDNA3.1(+)Neo-DeIg1 (B4DIVHv.1)-S (FIG. 13) and pcDNA3.1(+)Zeo-HuK (B4DIVKv.1)-S (FIG. 14).

The cDNAs are ligated into a plant expression vector having a zein gene promotor and a marker gene for selection, e.g., luciferase. The recombinant vectors are transformed into *E. coli* and transformants are screened for the presence of the Ig cDNA, as described above. Young maize seedings are transformed with the plasmids from the positive *E. coli* transformants by particle bombardment. Particle preparation, DNA coating, the bombardment with a PDS1000/He device (Bio-Rad Laboratories, Hercules Calif.), and selection of transformants by fluorometric measurements of protein extracts is as described [55].

Separate transgenic maize plants are generated from the positive embryos and grown to maturity. These are then cross-pollinated to produce plants that produce complete deimmunized B4 antibody. Selection and characterization of the antibodies is as described above.

TABLE 1

NEUTRALIZING ACTIVITIES OF DEIMMUNIZED B4 ANTIBODIES, DIVHV.1-4/V V.1 PRODUCED BY NS0 CELLS

| HIV-1 isolate | Clade | B4 Antibody | Antibody Conc (μg/ml) at 50% Inhibition |
|---|---|---|---|
| VL135 (PBL) | B | DIVHv.1/V v.1 | 0.21 |
| | | DIVHv.2/V v.1 | 0.53 |
| | | DIVHv.3/V v.1 | 0.26 |
| | | DIVHv.4/V v.1 | 0.26 |
| | | murine mAb B4 | 0.16 |
| ZIM748 (PBL) | C | DIVHv.1/V v.1 | 0.45 |
| | | DIVHv.2/V v.1 | 0.63 |
| | | DIVHv.3/V v.1 | 0.42 |
| | | DIVHv.4/V v.1 | 0.28 |
| | | murine mAb B4 | 0.21 |
| UG029 (PBL) | A | DIVHv.1/V v.1 | 0.47 |
| | | DIVHv.2/V v.1 | 0.79 |
| | | DIVHv.3/V v.1 | 0.63 |
| | | DIVHv.4/V v.1 | 0.35 |
| | | murine mAb B4 | 0.44 |
| UG046 (PBL) | D | DIVHv.1/V v.1 | 2.10 |
| | | DIVHv.2/V v.1 | 0.98 |
| | | DIVHv.3/V v.1 | 0.99 |
| | | DIVHv.4/V v.1 | 1.10 |
| | | murine mAb B4 | 0.40 |
| UG266 (PBL) | D | DIVHv.1/V v.1 | 0.82 |
| | | DIVHv.2/V v.1 | 1.20 |
| | | DIVHv.3/V v.1 | 2.20 |
| | | DIVHv.4/V v.1 | 7.00 |
| | | murine mAb B4 | 0.40 |
| TH036 (PBL) | E | DIVHv.1/V v.1 | 0.31 |
| | | DIVHv.2/V v.1 | 0.50 |
| | | DIVHv.3/V v.1 | 0.58 |
| | | DIVHv.4/V v.1 | 0.35 |
| | | murine mAb B4 | 0.25 |

TABLE 1-continued

NEUTRALIZING ACTIVITIES OF DEIMMUNIZED B4 ANTIBODIES, DIVHV.1-4/V V.1 PRODUCED BY NS0 CELLS

| HIV-1 isolate | Clade | B4 Antibody | Antibody Conc (μg/ml) at 50% Inhibition |
|---|---|---|---|
| MN (H9 cells) | B | DIVHv.1/V v.1 | >100 |
| | | DIVHv.2/V v.1 | >100 |
| | | DIVHv.3/V v.1 | >100 |
| | | DIVHv.4/V v.1 | >100 |
| | | murine mAb B4 | 14 |

TABLE 2

NEUTRALIZING ACTIVITIES OF DEIMMUNIZED B4 ANTIBODIES, DIVHV.1-4/V V.2-3 PRODUCED BY NS0 CELLS

| HIV-1 isolate | Clade | B4 Antibody | Antibody Conc (μg/ml) at 50% Inhibition |
|---|---|---|---|
| VL135 (PBL) | B | DIVHv.1/V v.2 | 0.24 |
| | | DIVHv.2/V v.2 | 0.23 |
| | | DIVHv.3/V v.2 | 0.35 |
| | | DIVHv.4/V v.2 | 0.30 |
| | | DIVHv.1/V v.3 | 0.39 |
| | | DIVHv.2/V v.3 | 0.67 |
| | | DIVHv.3/V v.3 | 0.62 |
| | | DIVHv.4/V v.3 | 0.48 |
| | | murine mAb B4 | 0.17 |
| UG029 (PBL) | A | DIVHv.1/V v.2 | 0.73 |
| | | DIVHv.2/V v.2 | 0.73 |
| | | DIVHv.3/V v.2 | 0.92 |
| | | DIVHv.4/V v.2 | 0.48 |
| | | DIVHv.1/V v.3 | 1.00 |
| | | DIVHv.2/V v.3 | 1.20 |
| | | DIVHv.3/V v.3 | 1.10 |
| | | DIVHv.4/V v.3 | 1.10 |
| | | murine mAb B4 | 0.28 |
| TH036 (PBL) | E | DIVHv.1/V v.2 | 0.51 |
| | | DIVHv.2/V v.2 | 0.63 |
| | | DIVHv.3/V v.2 | 0.70 |
| | | DIVHv.4/V v.2 | 0.32 |
| | | DIVHv.1/V v.3 | 0.77 |
| | | DIVHv.2/V v.3 | 0.62 |
| | | DIVHv.3/V v.3 | 0.44 |
| | | DIVHv.4/V v.3 | 0.63 |
| | | murine mAb B4 | 0.24 |

TABLE 3

NEUTRALIZING ACTIVITIES OF DEIMMUNIZED B4 ANTIBODIES, DIVHV.1V V.1 PRODUCED BY CHO CELLS (CLONES #7 AND #21)

| HIV-1 isolate | Clade | B4 Antibody | Antibody Conc (μg/ml) at 50% Inhibition |
|---|---|---|---|
| UG029 | A | DIVHv.1/V v.1 #7 | 0.25 |
| | | DIVHv.1/V v.1 #21 | 0.30 |
| | | murine mAb B4 | 0.31 |
| 23135 | B | DIVHv.1/V v.1 #7 | 0.032 |
| | | DIVHv.1/V v.1 #21 | 0.089 |
| | | murine mAb B4 | 0.12 |
| ZA/98/009 | C | DIVHv.1/V v.1 #7 | 0.022 |
| | | DIVHv.1/V v.1 #21 | 0.015 |
| | | murine mAb B4 | 0.033 |
| UG046 | D | DIVHv.1/V v.1 #7 | 0.22 |
| | | DIVHv.1/V v.1 #21 | 0.68 |
| | | murine mAb B4 | 0.43 |
| TH036 | E | DIVHv.1/V v.1 #7 | 0.22 |
| | | DIVHv.1/V v.1 #21 | 0.68 |
| | | murine mAb B4 | 0.43 |
| CM235 | E | DIVHv.1/V v.1 #7 | 0.021 |
| | | DIVHv.1/V v.1 #21 | 0.022 |
| | | murine mAb B4 | 0.022 |

TABLE 4

IN VITRO CYTOKINE RESPONSES INDUCED BY MAB B4 & ITS DEIMMUNIZED COUNTERPARTS

| Antigen in culture | Cytokine conc in 2 × 10$^6$ PBMC culture (ng/ml) | | | | |
|---|---|---|---|---|---|
| | IFN-γ | IL-2 | TNF-α | IL-4 | IL-10 |
| PWM | >5.0 | >5.0 | 0.43 | BDL$^d$ | >0.93 |
| B4$^a$ | BDL$^d$ | BDL$^d$ | 0.36 | BDL$^d$ | 0.68 |
| DH1DK1CHO#16$^b$ | BDL$^d$ | BDL$^d$ | BDL$^d$ | BDL$^d$ | BDL$^d$ |
| DH1DK1CHO#7$^c$ | BDL$^d$ | BDL$^d$ | BDL$^d$ | BDL$^d$ | BDL$^d$ |

$^{a,\ b\ \&\ c}$monoclonals added to cultures at 10.0 μg/ml
$^d$BDL, below detection level

---

We claim:

1. A deimmunized recombinant monoclonal antibody expressed from the fusion of nucleic acids encoding a deimmunized Fv fragment of a murine antibody B4 comprising $V_H$ and Vκ variable chains and complementarity determining regions of the variable chains of said murine antibody B4 SEQ ID NOS: 20, 22, 24, 26, 28 and 30 and nucleic acids encoding human immunoglobulin constant regions, wherein said deimmunized Fv fragment of murine antibody B4 is deimmunized by replacing the murine heavy $V_H$ chain from the Fv domains of said murine antibody B4 with a nucleotide sequence encoding a deimmunized $V_H$ chain of murine antibody B4 selected from the group consisting of DIVHv.1 of SEQ ID NO: 5, DIVHv.2 of SEQ ID NO: 6, DIVHv.3 of SEQ ID NO: 7, and DIVHv.4 of SEQ ID NO: 8 and replacing the Vκ chain from the Fv domains of said murine antibody B4 with a nucleotide sequence encoding a deimmunized Vκ chain of murine antibody B4 selected from the group consisting of DIVKv.1 of SEQ ID NO: 9, DIVKv.2 of SEQ ID NO: 10 and DIVKv.3 of SEQ ID NO: 11.

2. A recombinant host cell which secretes the deimmunized monoclonal antibody of claim 1., 3. A deimmunized aglycosylated monoclonal antibody according to claim 1, wherein $Asn_{297}$ of the human immunoglobulin constant region is N-aglycosylated by replacing the AAC codon for Asn with the CAC codon for His.

4. A deimmunized monoclonal antibody comprising heavy variable chain of SEQ ID NO: 5 and light variable chain of SEQ ID NO: 9.

5. A deimmunized aglycosylated monoclonal antibody comprising heavy variable chain of SEQ ID NO: 5 and the light variable chain of SEQ ID NO: 9, wherein $Asn_{297}$ of the human immunoglobulin constant region is N-aglycosylated by replacing the AAC codon for Asn with the CAC codon for His.

6. A recombinant host cell which secretes the deimmunized aglycosylated antibody of claim 3.

7. A deimmunized monoclonal antibody of claim 1, wherein the human immunoglobulin is IgG1.

* * * * *